(12) United States Patent
Hentsch et al.

(10) Patent No.: US 7,892,833 B2
(45) Date of Patent: Feb. 22, 2011

(54) USING INHIBITORS OF HISTONE DEACETYLASES FOR THE SUPPRESSION THERAPY OF INHERITED DISEASE PREDISPOSING CONDITIONS

(75) Inventors: Bernd Hentsch, Frankfurt am Main (DE); Alexander B. Maurer, Bad Homburg (DE); Sascha Hövelmann, Frankfurt am Main (DE); Monika Raab, Ronneburg (DE); Elke Martin, Karlsruhe (DE)

(73) Assignee: TopoTarget Germany AG, Frankfurt am Main (DE)

( * ) Notice: Subject to any disclaimer, the term of this patent is extended or adjusted under 35 U.S.C. 154(b) by 960 days.

(21) Appl. No.: 11/275,263

(22) Filed: Dec. 21, 2005

(65) Prior Publication Data

US 2007/0037738 A1    Feb. 15, 2007

Related U.S. Application Data

(63) Continuation of application No. PCT/EP2004/006797, filed on Jun. 23, 2004.

(30) Foreign Application Priority Data

Jun. 25, 2003   (EP) ................................ 03014278

(51) Int. Cl.
  *C12N 15/01*  (2006.01)
  *G01N 33/53*  (2006.01)
(52) U.S. Cl. ........................................ 435/444; 435/7.71
(58) Field of Classification Search ........................ None
   See application file for complete search history.

(56) References Cited

U.S. PATENT DOCUMENTS

| 2005/0038113 A1 | 2/2005 | Groner et al. |
| 2006/0160897 A1 | 7/2006 | Pelicci et al. |
| 2008/0207724 A1 | 8/2008 | Mink et al. |
| 2009/0186809 A1 | 7/2009 | Hentsch et al. |

FOREIGN PATENT DOCUMENTS

| DE | EP-1293205 A1 * | 9/2001 |
| EP | 1 293 205 | 3/2003 |
| WO | WO00/66096 | 11/2000 |
| WO | WO02/102989 | 12/2002 |
| WO | WO2004/017996 | 3/2004 |

OTHER PUBLICATIONS

Romeo-Gimenez, 2008, Int. J. Cancer, 122, 1422-1425.*
Gottlicher, 2001, The EMBO Journal, 20, 6969-6978.*
Truta, 2005, Familial Cancer, 4, 127-133.*
Varesco, 2004, Tech Coloproctol, 8, S305-S308.*
Bougatef, 2007, Gastroenterologie Clinique et Biologique, 31, 1062-1066 (Abstract only), 2 pages.*
Shoji, 1993, Surgery, 113, 560-563.*
[Retrived from] http://web.archive.org/web/20020417140826/http://www.genetichealth.com/CRC_FAP_A_Hereditary_Syndrome.shtml, 2002, 3 pages [Retrieved on Jul. 27, 2009].*
Henderson, 2002, The Journal of Biological Chemistry, 277, 24258-24264.*
International Preliminary Report on Patentability for PCT Appl. No. PCT/EP2004/006797 (Jan. 3, 2006).
Abdul, M., et al., "Inhibition by Anticonvulsants of Prostate-specific Antigen and Interleukin-6 Secretion by Human Prostate Cancer Cells," Anticancer Res. 2001;21:2045-2048.
Mirnikjoo, B., et al., "Protein Kinase Inhibition by ω-3 Fatty Acids," J. Biol. Chem. 2001;276(14):10888-10896.
Murphy, D. G., et al., "Inhibition Studies on Chicken Muscle Aldose Reductase," Biochem. Pharmacol. 1985;34(16):2961-2965.
Olsen, C. M., et al., "Antiepilectic drugs inhibit cell growth in the human breast cancer cell line MCF7," Mol. Cell. Endocrinol. 2004;213:173-179.
Papdimitriou, A., et al., "Late Onset Lipid Storage Myopathy Due to Multiple Acyl CoA Dehydrogenase Deficiency Triggered by Valproate," Neuromus. Dis. 1991;1(4):247-252.
Park-Matsumoto, Y., et al., "Valproate induced lupus-like syndrome," J. Neurol. Sci. 1996;143:185-186.
Poulsom, R., "Inhibition of Hexonate Dehydrogenase and Aldose Reductase from Bovine Retina by Sorbinil, Statil, M79175 and Valproate," Biochem. Pharmcol. 1986;35(17):2955-2959.
Sims, K. B., "Von Hippel-Lindau disease: gene to bedside," Curr. Op. Neurol. 2001;14:695-703.
Song, C. H., et al., "Successful Treatment of Steroid-Resistant Chorea Associated with Lupus by Use of Valproic Acid and Clonidine-HCL Patch," Clin. Ped. 1997;36(11):659-662.
Turnbull, D. M., et al., "The Effect of Valproate on Blood Metabolite Concentrations in Spontaneously Diabetic, Ketoacidotic, BB/E Wistar Rats," Diabetes Res. 1985;2:45-48.
Xiao, T., et al., "Inhibition of Rabbit Dermal Fibroblast Proliferation with Natrii Valproas," Database Biosis [Online], Bioscience Information Service, Philadelphia, PA, US; 1992; Database accession No. 1992:502361 abstract & Hunan Yike Daxue Xuebao, vol. 17, No. 2, pp. 173-175.
International Search Report for PCT App. No. PCT/EP2004/006797 (Feb. 11, 2005).
Written Opinion for PCT App. No. PCT/EEP2004/006797.

* cited by examiner

*Primary Examiner*—Andrew D Kosar
*Assistant Examiner*—Satyanarayana R Gudibande
(74) *Attorney, Agent, or Firm*—Shelly Guest Cermak; Cermak Nakajima LLP

(57) ABSTRACT

Compounds can be used to act as inhibitors of enzymes having histone deacetylase activity for the medical therapy of conditions which predispose a person for the development of a disease, such as but not limited to cancer, inflammatory or metabolic diseases. Such conditions are linked to genetically inherited mutations of crucial genes which predispose a person with this condition to develop the disease phenotype. Thus, such compounds can be used for a suppressive therapeutic approach—the SUPPRESSION THERAPY—in order to inhibit or delay the onset or progression of the genetically predisposed disorder. Furthermore, a clinically used medicament can be manufactured for the SUPPRESSION THERAPY of such inherited predisposing conditions.

13 Claims, 12 Drawing Sheets

Figure 1

| Syndrome | Cloned Gene | Cell line (Culture medium) | Mutation |
|---|---|---|---|
| Li-Fraumeni Syndrome | P53 tumor suppressor | MDAH041 Li-Fraumeni Fibroblasts (DMEM, 10% FBS) | p53 null |
| Familial Retinoblastoma | RB1 tumor suppressor | WERI-Rb-1 (RPMI 1640, 10% FBS) Y79 (RPMI 1640, 10% FBS, 2mM Glutamine) | Deletion of RB1 Mutation in RB1 Derived from human retinoblastoma |
| Wilms Tumor | WT1 tumor suppressor | G-401 (McCoy's 5a, 10% FBS, 1.5 mM L-glutamine) | Deletion of 11p13 |
| Neurofibromatosis Type 1 | NF1 protein=neurofibromin 1 tumor suppressor | Immortalized Schwann cells from NF1 deficient mice (Iscove's modified DMEM, 5% FCS) | NF1 deficient |
| Neurofibromatosis Type 2 | NF2 protein = merlin or neurofibromin 2 tumor suppressor | HEI193 (Modified DMEM/F12, 10% FBS) | Splice site mutation of NF2 |
| Familial Adenomatous Polyposis | APC tumor suppressor | HT29 (adenocarcinoma colon) (McCoy's 5a, 10% FBS, 2mM Glutamine) SW626 (ovarian cancer) (RPMI 1640, 10% FBS) SW480 (adenocarcinoma colon) (DMEM, 10% FBS) | Carboxyl terminal-truncated APC protein A2941 insertion leading to truncation of APC truncation of APC |
| Tuberous sclerosis 1 | TSC1 protein = hamartin tumor suppressor | HCV29 (RPMI 1640, 10% FBS) | Nonsense mutation Q55X |
| Tuberous sclerosis 2 | TSC2 protein = tuberin tumor suppressor | tsc2 ang1 (mouse) (DMEM, 10% FBS, 4 mM L-glutamine, 1.5 g/L sodium bicarbonate) | Tsc2+/- |
| Deleted in Pancreatic Carcinoma 4 | DPC4 also known as Smad4 tumor suppressor | BxPC-3 (RPMI 1640, 10% FBS, 2mM L-glutamine, 1.5 g/L sodium bicarbonate, 4.5 g/L glucose, 10 mM Hepes, 1mM sodium pyruvate) Capan-1 (Iscove's modified Dulbecco's medium, 20% FBS, 4 mM L-glutamine, 1.5 g/L sodium bicarbonate) | Homozygous deletion Stop at codon 343 |

Figure 1 (continued)

| Deleted in Colorectal Carcinoma | DCC<br>tumor suppressor | MIA PaCa-2<br>(DMEM, 10% FBS, 2.5% HS, 4 mM L-glutamine, 1.5 g/L sodium bicarbonate, 4.5 g/L glucose) | Homozygous deletion |
|---|---|---|---|
| Familial Breast Cancer | BRCA1<br>tumor suppressor | HCC-1937<br>(RPMI 1640, 15% FBS) | BRCA1 deficient |
| Familial Breast Cancer | BRCA2<br>tumor suppressor | | |
| Peutz-Jeghers Syndrome | STK11<br>tumor suppressor<br>protein = serine-threonine kinase 11 | AsPC-1<br>(RPMI 1640, 10% FBS, 2mM L-glutamine, 1.5 g/L sodium bicarbonate, 4.5 g/L glucose, 10 mM Hepes, 1mM sodium pyruvate) | Silencing of STK11/LKB1 |
| Hereditary Nonpolyposis Colorectal Cancer type 1 HNPCC1 | MSH2<br>tumor suppressor | LoVo<br>(RPMI 1640, 10% FBS) | hMSH2 null |
| Hereditary Nonpolyposis Colorectal Cancer type 2 HNPCC2 | MLH1<br>tumor suppressor | HCT116<br>(McCoy's 5a, 10% FBS, 1.5 mM L-glutamine) | nonsense mutation in Exon 9 |
| von Hippel-Lindau Syndrome | VHL<br>tumor suppressor | human sporadic renal cell carcinoma 786-0<br>(DMEM, 10% FBS) | Mutation |
| Familial Melanoma | CDKN2A<br>protein = cyclin-dependent kinase inhibitor 2A<br>tumor suppressor | MM96L<br>(RPMI 1640, 10% FCS)<br><br>SK-Mel-13<br>(DMEM, 10% FBS)<br><br>253J (modified Eagle's MEM, 10% FBS, vitamins, pyruvate, L-glutamine, nonessential amino acids), RT112 (DMEM, 10% FBS, 2mM Glutamine, 1% Non Essential Amino Acids), SW1710 (DMEM, 15% FCS), UM-UC-3 (DMEM, 10% FCS), VM-CUB-2 (DMEM, 10% FBS), T24 (DMEM, 10% FCS) | No expression/ deletion<br><br>Homozygous deletion<br><br>Deletion<br><br><br><br>Deletion in chr. 9 |
| Gorlin Syndrome: Nevoid basal cell carcinoma syndrome (NBCCS) | PTCH<br>protein = patched<br>tumor suppressor | | |
| Multiple Endocrine Neoplasia Type 1 | MEN1<br>tumor suppressor | | |

Figure 1 (continued)

| | | | |
|---|---|---|---|
| Multiple Endocrine Neoplasia Type 2 | RET, MEN2 | | |
| Beckwith-Wiedmann Syndrome | p57, KIP2 | NCI H295R (DMEM/Ham's F-12 medium, sodium selenite (5 ng/ml), insulin (10 μg/ml), transferrin (5.5 μg/ml), ethanolamine (2 μg/ml), albumin (1 mg/ml), linoleic acid (9 μg/ml), HEPES (15 mM)) | Promoter regulation |
| Hereditary papillary renal cancer (HPRC) | MET | NIH3T3 cells stably expressing MET (DMEM, 10% FCS) | |
| Cowden syndrome | PTEN tumor suppressor | HCC1937 (RPMI 1640, 10% FBS, 2 mM L-glutamine, 1.5 g/L sodium bicarbonate, 4.5 g/L glucose, 10mM HEPES, 1mM sodium pyruvate) | PTEN deletion |
| Hereditary prostate cancer numerous loci: HPC1(PRCA1), HPCX, MXI1, KAI1, PCAP | HPC1 and PRCA1 are same designation ribonuclease L (RNaseL) maps to this locus | LNCaP (RPMI 1640, 10% FBS, 2 mM L-glutamine, 1.5 g/L sodium bicarbonate, 4.5 g/L glucose, 10 mM HEPES, 1mM sodium pyruvate)<br><br>DU145 (RPMI 1640, 10% FBS) | HPC1: 471delAAAG truncation<br><br>HPC1: Gly296Val |
| Ataxia telangiectasia (AT) | ATM | M059J (DMEM and Ham's F12 medium, 10% FBS, 2.5 mM L-glutamine, 15 mM HEPES, 0.5 mM sodium pyruvate, 1.2 g/L sodium bicarbonate, 0.05 mM non-essential amino acids and) | express two different aberrant ATM transcripts: 4776 del 133, 4909 ins 116 |
| Bloom syndrome | BLM | GM08505B (DMEM, 10% FBS) | BML$^{-/-}$ |
| Xeroderma pigmentosum (XP) 7 complementation groups | XPA - XPG | GM02415B (XPA), GM01630 (XPE) (DMEM, 15% serum (1:1 HS/FBS))<br><br>UV-20, UV-5, UV-24, UV-41, UV-135 (CHO cell lines) (DMEM, 6% serum (1:1 HS/FBS)) | Mutations/ Deletions<br><br>Mutations/ deletions |
| Fanconi's anemia 8 complementation groups | FANCA - FANCH | HSC99 (FA-A) (RPMI-1640, 10% FBS)<br><br>HSC536/N & PD149L (FA-C lymphocyte) (RPMI-1640, 10% FBS) | Mutation leading to defective protein<br><br>Homozygous mutation |

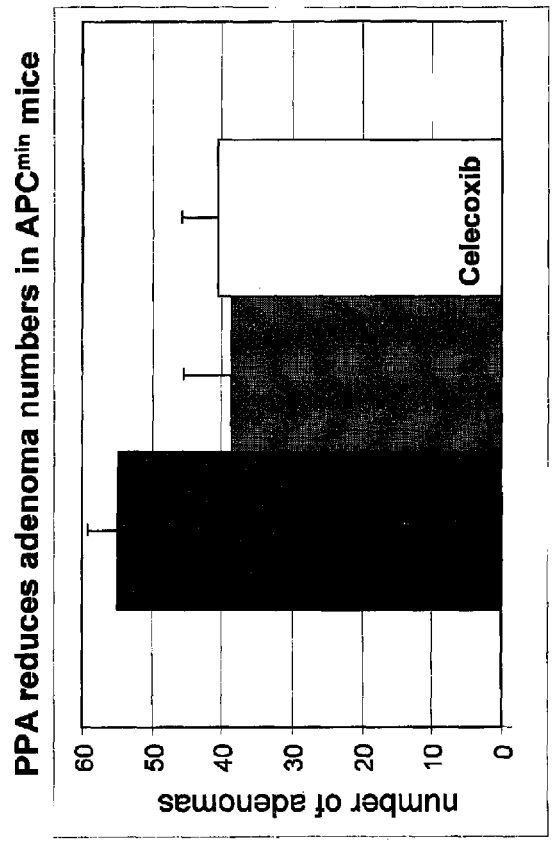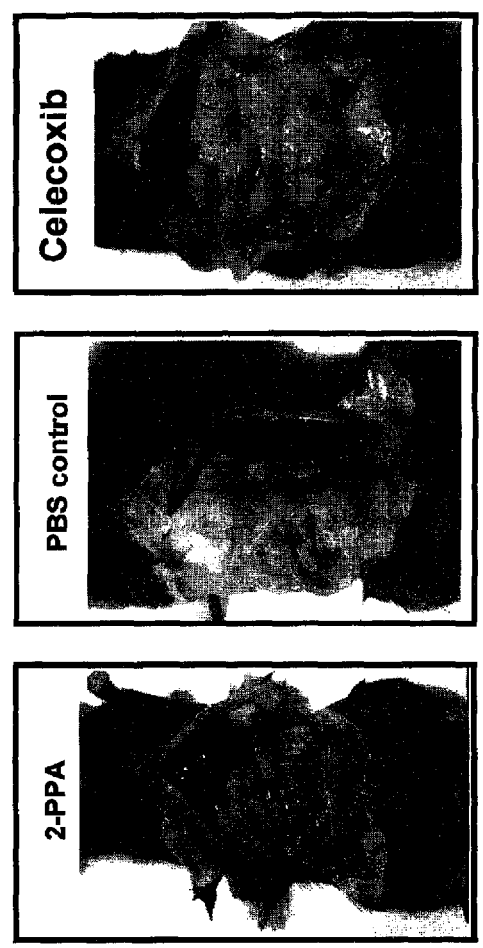
Figure 2

SEQUENCE LISTING

<160> NUMBER OF SEQ ID NOS: 20

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
ggtgaaggtc ggagtcaacg                                                   20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
caaagttgtc atggatgacc                                                   20

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
atgtacagga tgcaactcct                                                   20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
tcaagttagt gttgagatga                                                   20

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
atgggtctca cctcccaact                                                   20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
tcagctcgaa cactttgaat                                                   20

<210> SEQ ID NO 7
<211> LENGTH: 23

```
<212> TYPE: DNA
<213> ORGANISM: Artificial
<220> FEATURE:
<223> OTHER INFORMATION: Primer

<400> SEQUENCE: 7
atgaggatgc ttctgcattt gag                                                 23

<210> SEQ ID NO 8
<211> LENGTH: 22
<212> TYPE: DNA
<213> ORGANISM: Artificial
<220> FEATURE:
<223> OTHER INFORMATION: Primer

<400> SEQUENCE: 8
tccactcggt gttcattaca cc                                                  22

<210> SEQ ID NO 9
<211> LENGTH: 24
<212> TYPE: DNA
<213> ORGANISM: Artificial
<220> FEATURE:
<223> OTHER INFORMATION: Primer

<400> SEQUENCE: 9
atgaactcct tctccacaag cgcc                                                24

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
ctacatttgc cgaagagccc tcag                                                24

<210> SEQ ID NO 11
<211> LENGTH: 23
<212> TYPE: DNA
<213> ORGANISM: Artificial
<220> FEATURE:
<223> OTHER INFORMATION: Primer

<400> SEQUENCE: 11
atgacttcca agctggccgt ggc                                                 23

<210> SEQ ID NO 12
<211> LENGTH: 22
<212> TYPE: DNA
<213> ORGANISM: Artificial
<220> FEATURE:
<223> OTHER INFORMATION: Primer

<400> SEQUENCE: 12
ttatgaattc tcagccctct tc                                                  22

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
```
ttgcctggtc ctcctgactg                                               20

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
gatgtctggg tcttggttct                                               20

<210> SEQ ID NO 15
<211> LENGTH: 24
<212> TYPE: DNA
<213> ORGANISM: Artificial
<220> FEATURE:
<223> OTHER INFORMATION: Primer

<400> SEQUENCE: 15
atgtgtcacc agcagttggt catc                                          24

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
ctatagtagc ggtcctgggc                                               20

<210> SEQ ID NO 17
<211> LENGTH: 24
<212> TYPE: DNA
<213> ORGANISM: Artificial
<220> FEATURE:
<223> OTHER INFORMATION: Primer

<400> SEQUENCE: 17
atgagcactg aaagcatgat ccgg                                          24

<210> SEQ ID NO 18
<211> LENGTH: 22
<212> TYPE: DNA
<213> ORGANISM: Artificial
<220> FEATURE:
<223> OTHER INFORMATION: Primer

<400> SEQUENCE: 18
tcacagggca atgatcccaa ag                                            22

<210> SEQ ID NO 19
<211> LENGTH: 29
<212> TYPE: DNA
<213> ORGANISM: Artificial
<220> FEATURE:
<223> OTHER INFORMATION: Primer

<400> SEQUENCE: 19
atgaaatata caagttatat cttggcttt                                     29

<210> SEQ ID NO 20
<211> LENGTH: 20
<212> TYPE: DNA
<213> ORGANISM: Artificial

```
<220> FEATURE:
<223> OTHER INFORMATION: Primer

<400> SEQUENCE: 20
ttactgggat gctcttcgac                                                    20
```

USING INHIBITORS OF HISTONE DEACETYLASES FOR THE SUPPRESSION THERAPY OF INHERITED DISEASE PREDISPOSING CONDITIONS

This application is a Continuation of, and claims priority under 35 U.S.C. §120 to, International application number PCT/EP2004/006797, filed 23 Jun. 2004, and claims priority under 35 U.S.C. §119 to European application number 03014278.0, filed 25 Jun. 2003, the entireties of both of which are incorporated by reference herein. Also, the Sequence Listing filed on compact disk herewith is hereby incorporated by reference (filename: 033-006 Seq List; file size: 4 kb; date created: Dec. 21, 2005).

BACKGROUND OF THE INVENTION

1. Field of the Invention

The present invention relates to the use of compounds acting as inhibitors of enzymes having histone deacetylase activity for the medical therapy of conditions which predispose a person for the development of a disease, such as but not limited to cancer, inflammatory or metabolic diseases. Such conditions are linked to genetically inherited mutations of crucial genes which predispose a person with this condition to develop the disease phenotype. Thus, the invention relates to the use of such compounds for a suppressive therapeutic approach—the SUPPRESSION THERAPY—in order to inhibit or delay the onset or progression of the genetically predisposed disorder. Furthermore, the invention includes the manufacture of a clinically used medicament for the SUPPRESSION THERAPY of such inherited predisposing conditions.

Current progress in the understanding of the molecular biology of pathogenic processes such as modern tumor biology has provided insights into the genetic basis and into the fundamental biochemical pathways of the development of many diseases, e.g., of cancerogenesis. These newly identified mechanisms offer new opportunities for therapeutic intervention not only in the management of the acute disease state, but also for the medical management of a pre-symptomatic condition using an approach which herein is referred to as Suppression Therapy. Such a condition is defined by the inherited presence of gene mutations or critical gene polymorphisms which predispose a person to develop the disease phenotype. Suppression therapy is a novel concept, which refers to the inhibition or delay of pathogenesis through the use of naturally occurring or synthetic compounds and drugs which display such suppressive properties, e.g., by suppression of the mechanisms caused by such inherited genetic mutations, and thus, suppression of diseased signal transductions and the development of the disease phenotype.

In this invention, we propose the use of inhibitors of enzymes having histone deacetylase activity in medical suppression therapy of a set of human conditions, which are based on inherited mutations that predispose a person to develop a disorder and in which the development of the disease is linked to the presence of such mutations or polymorphisms.

2. Brief Description of the Related Art

Chromatin Regulation and Disease

Local remodeling of chromatin is a key step in the transcriptional activation of genes. Dynamic changes in the nucleosomal packaging of DNA must occur to allow transcriptional proteins to make contact with the DNA template. One of the most important mechanisms influencing chromatin remodeling and gene transcription are posttranslational modifications of histones and other cellular proteins by acetylation and subsequent changes in chromatin structure (Davie, 1998, Curr Opin Genet Dev 8, 173-8; Kouzarides, 1999, Curr Opin Genet Dev 9, 40-8; Strahl and Allis, 2000, Nature 403, 41-4). In the case of histone hyperacetylation, changes in the electrostatic attraction of DNA and steric hindrance introduced by the hydrophobic acetyl group leads to destabilisation of the interaction of histones with DNA. As a result, acetylation of histones disrupts nucleosomes and allows the DNA to become accessible to the transcriptional machinery. Removal of the acetyl groups allows the histones to bind more tightly to DNA and to adjacent nucleosomes, and thus, to maintain a transcriptionally repressed chromatin structure. Acetylation is mediated by a series of enzymes with histone acetyltransferase (HAT) activity. Conversely, acetyl groups are removed by specific histone deacetylase (HDAC) enzymes. Disruption of these mechanisms gives rise to transcriptionally misguided regulation and may contribute to a variety of human diseases, including autoimmune, inflammatory, metabolic or hyperproliferative disorders, including tumorigenic transformation and tumor progression.

Additionally, other molecules such as transcription factors alter their activity and stability depending on their acetylation status. E.g. PML-RAR, the fusion protein associated with acute promyelocytic leukemia (APL) inhibits p53 through mediating deacetylation and degradation of p53, thus allowing APL blasts to evade p53 dependent cancer surveillance pathways. Expression of PML-RAR in hematopoietic precursor cells results in repression of p53 mediated transcriptional activation and protection from p53-dependent apoptosis triggered by genotoxic stresses (X-rays, oxidative stress). However, the function of p53 is reinstalled in the presence of HDAC inhibitors implicating active recruitment of HDAC to p53 by PML-RAR as the mechanism underlying p53 inhibition (Insinga et al., February 2004, EMBO Journal, 1-11). Therefore, acetylation of proteins distinct from histones, such as acetylation of p53, plays a crucial role in the anti-disease activity of HDAC inhibitors.

Nuclear Receptors and Histone Deacetylases

Nuclear hormone receptors are ligand-dependent transcription factors that control development and homeostasis through both positive and negative control of gene expression. Defects in these regulatory processes underlie the causes of many diseases and play an important role in the development of cancer. Many nuclear receptors, including T3R, RAR and PPAR, can interact with corepressors, such as N-CoR and SMRT, in the absence of a ligand and thereby inhibit transcription. Furthermore, N-CoR has also been reported to interact with antagonist-occupied progesterone and estrogen receptors. Most interestingly, N-CoR and SMRT have been shown to exist in large protein complexes, which also contain mSin3 proteins and histone deacetylases (Pazin and Kadonaga, 1997; Cell 89, 325-8). Thus, the ligand-induced switch of nuclear receptors from repression to activation reflects the exchange of corepressor and coactivator complexes with antagonistic enzymatic activities.

Gene Regulation by Nuclear Receptors

Such corepressor complexes which contain HDAC activity, not only mediate repression by nuclear receptors, but also interact with additional transcription factors including Mad-1, BCL-6, and ETO. Many of these proteins play key roles in disorders of cell proliferation and differentiation (Pazin and Kadonaga, 1997, Cell 89, 325-8; Huynh and Bardwell, 1998, Oncogene 17, 2473-84; Wang, J. et al., 1998, Proc Natl Acad Sci U S A 95, 10860-5). T3R for example was originally identified on the basis of its homology with the viral oncogene v-erbA, which in contrast to the wild type receptor does not bind a ligand and functions as a constitutive repressor of transcription. Furthermore, mutations in RARs have been associated with a number of human cancers, particularly acute promyelocytic leukemia (APL) and hepatocellular carcinoma. In APL patients RAR fusion proteins resulting from chromosomal translocations involve either the promyelocytic leukemia protein (PML) or the promyelocytic zinc finger protein (PLZF). Although both fusion proteins can interact with components of the corepressor complex, the addition of retinoic acid dismisses the corepressor complex from PML-RAR, whereas PLZF-RAR interacts constitutively. These findings provide an explanation why PML-RAR APL patients achieve complete remission following retinoic acid treatment whereas PLZF-RAR APL patients respond very poorly (Grignani et al., 1998, Nature 391, 815-8; Guidez et al., 1998, Blood 91, 2634-42; He et al., 1998, Nat Genet 18, 126-35; Lin et al., 1998, Nature 391, 811-4).

Recently, a PML-RAR patient who had experienced multiple relapses after treatment with retinoic acid has been treated with the HDAC inhibitor phenylbutyrate, resulting in complete remission of the leukemia (Warrell et al., 1998, J. Natl. Cancer Inst. 90, 1621-1625).

The Protein Family of Histone Deacetylases

The recruitment of histone acetyltranferases (HATs) and histone deacetylases (HDACs) is considered as a key element in the dynamic regulation of many genes playing important roles in cellular proliferation and differentiation. Hyperacetylation of the N-terminal tails of histones H3 and H4 correlates with gene activation whereas deacetylation can mediate transcriptional repression. Consequently, many diseases have been linked to changes in gene expression caused by mutations affecting transcription factors. Aberrant repression by leukemia fusion proteins such as PML-RAR, PLZF-RAR, AML-ETO, and Stat5-RAR serves as a prototypical example in this regard. In all of these cases, chromosomal translocations convert transcriptional activators into repressors, which constitutively repress target genes important, e.g., for hematopoietic differentiation via recruitment of HDACs. It is plausible that similar events could also contribute to pathogenesis in many other types of diseases. There is growing evidence that the same holds true also for autoimmune, inflammatory, metabolic or hyperproliferative disorders.

Mammalian histone deacetylases can be divided into three subclasses (Gray and Ekström, 2001). HDACs 1, 2, 3, and 8 which are homologues of the yeast RPD3 protein constitute class I. HDACs 4, 5, 6, 7, 9, and 10 are related to the yeast Hda 1 protein and form class II. Recently, several mammalian homologues of the yeast Sir2 protein have been identified forming a third class of deacetylases which are NAD dependent. Furthermore, HDAC 11 has been classified as a class I histone deacetylase with structural features of a class II HDAC. All of these HDACs appear to exist in the cell as subunits of a plethora of multiprotein complexes. In particular, class I and II HDACs have been shown to interact with transcriptional corepressors mSin3, N-CoR and SMRT which serve as bridging factors required for the recruitment of HDACs to transcription factors.

Therapy with HDAC Inhibitors

Additional clinical investigations have recently been initiated to exploit the systemic clinical treatment of cancer patients based on the principle of HDAC inhibition. By now, a clinical phase II trial with the closely related butyric acid derivative Pivanex (Titan Pharmaceuticals) as a monotherapy has been completed demonstrating activity in stage III/IV non-small cell lung cancer (Keer et al., 2002, ASCO, Abstract No. 1253). More HDAC inhibitors have been identified, with NVP-LAQ824 (Novartis) and SAHA (Aton Pharma Inc.) being members of the structural class of hydroxamic acids tested in phase II clinical trials (Marks et al., 2001, Nature Reviews Cancer 1, 194-202). Another class comprises cyclic tetrapeptides, such as depsipeptide (FR901228—Fujisawa) used successfully in a phase II trial for the treatment of T-cell lymphomas (Piekarz et al., 2001, Blood 98, 2865-8). Furthermore, MS-27-275 (Mitsui Pharmaceuticals), a compound related to the class of benzamides, is now being tested in a phase I trial treating patients with hematological malignancies.

2-propyl-pentanoic acid 2-propyl-pentanoic acid (2PPA) has multiple biological activities which depend on different molecular mechanisms of action:

2PPA is an antiepileptic drug.

2PPA is teratogenic. When used as an antiepileptic drug during pregnancy, 2PPA can induce birth defects (neural tube closure defects and other malformations) in a few percent of born children. In mice, 2PPA is teratogenic in the majority of mouse embryos when properly dosed.

2PPA activates a nuclear hormone receptor (PPARδ). Several additional transcription factors are also derepressed, but some factors are not significantly derepressed (glucocorticoid receptor, PPARα).

2PPA occasionally causes hepatotoxicity, which may depend on poorly metabolized esters with coenzyme A.

2PPA is an inhibitor of HDACs.

The use of 2PPA derivatives allowed to determine that the different activities are mediated by different molecular mechanisms of action. Teratogenicity and antiepileptic activity follow different modes of action because compounds could be isolated which act either preferentially teratogenic or preferentially antiepileptic (Nau et al., 1991, Pharmacol. Toxicol. 69, 310-321). Activation of PPARδ was found to be strictly correlated with teratogenicity (Lampen et al., 1999, Toxicol. Appl. Pharmacol. 160, 238-249) suggesting that, both, PPARδ activation and teratogenicity require the same molecular activity of 2PPA. Also, differentiation of F9 cells strictly correlated with PPARδ activation and teratogenicity as suggested by Lampen et al., 1999, and documented by the analysis of differentiation markers (Werling et al., 2001, Mol. Pharmacol. 59, 1269-1276). It was shown, that PPARδ activation is caused by the HDAC inhibitory activity of 2PPA and its derivatives (WO 02/07722 A2; WO 03/024442 A2). Furthermore, it was shown that the established HDAC inhibitor TSA activates PPARδ and induces the same type of F9 cell differentiation as 2PPA. From these results it can be concluded that not only activation of PPARδ but also induction of F9 cell differentiation and teratogenicity of 2PPA or 2PPA derivatives are caused by HDAC inhibition.

Antiepileptic and sedating activities follow different structure activity relationships and thus obviously depend on a primary 2PPA activity distinct from HDAC inhibition. The mechanism of hepatotoxicity is poorly understood and it is unknown whether it is associated with formation of the 2PPA-CoA ester. HDAC inhibition, however, appears not to require CoA ester formation.

2PPA as an Inhibitor of Histone Deacetylases

2PPA has been developed as a drug used for the treatment of epilepsy. Accordingly, 2PPA is used systemically, orally, or intravenously, to allow the drug to pass the blood brain barrier to reach the epileptic target regions in the brain tissue in order to fulfill its anti-epileptic mission. Moreover, 2PPA has been shown to potentially possess particular beneficial effects when used for the treatment of many different types of human cancers as a single agent or in combination with a whole variety of other anti-tumor therapies which are individually based on strikingly different modes of action, by inhibiting specific sets of enzymes having HDAC activity and thereby inducing differentiation and/or apoptosis (WO 02/07722 A2, EP 1170008; WO 03/024442 A2, EP 1293205 A1). For the treatment or prevention of malignant diseases, autoimmune diseases, or other inflammatory or hyperproliferative disorders, 2PPA may also be administered systemically, orally, or intravenously. Furthermore, it was shown, that 2PPA permeates human skin effectively and therefore can be administered topically on skin exhibiting beneficial effects when used for the topical treatment or prevention of autoimmune, inflammatory or hyperproliferative human skin diseases, e.g., psoriasis and human skin cancer (EP application No. 03014278.0). This new potential of 2PPA, and other HDAC inhibitors, to act as immune modulating compounds supports this invention to employ these compounds as anti-inflammatory drugs for the therapy of disorders linked to pathologically overactive immune cells.

SUMMARY OF THE INVENTION

The present invention aims at providing means for the prevention or treatment of genetically inherited human diseases.

To this end, it was now found that 2PPA has in fact unexpected beneficial effects when used for the suppressive therapy of genetically inherited predispositions for the development of disorders which are based on inherited mutations of important gene loci, e.g., of tumor suppressor genes (including, but not limited to, p53, pRB, PTEN, p21, p57, WT1, NF1, NF2, APC, TSC1, TSC2, BRCA1 and BRCA2), genes controlling the immune system, in particular immune responses, activated oncogene mutations such as of tyrosine kinase receptors or the like, and also mutations in transcription factor complexes, such as stabilizing mutations of beta-catenin (Polakis et al.; Genes & Development, Aug 1; 14(15): 1837-51, 2000) which in fact may predispose a person to the development of a broad variety of tumor diseases. Such mutations of beta-catenin are expected to cause an enhanced expression of an HDAC isoenzyme, namely HDAC-2, frequently found to be upregulated in human cancer, particularly in colorectal cancers.

The present invention therefore relates to the use of a histone deacetylase inhibitor for the manufacture of a medicament for the treatment of an inherited condition which predisposes a person for the development of a disease. The invention further relates to the use of a histone deacetylase inhibitor for the manufacture of a medicament for the treatment or prevention of an inherited disease wherein the treatment or prevention comprises administering the medicament to an individual having an inherited condition predisposing him/her for the development of the inherited disease. The invention further relates to the use of a histone deacetylase inhibitor for the manufacture of a medicament for the treatment of an individual suffering from a disease which is associated with an inherited condition predisposing the individual to develop the disease.

A histone deacetylase inhibitor is a compound capable of inhibiting the histone deacetylase activity of at least one enzyme having histone deacetylase activity. Preferred histone deacetylase inhibitors are described infra.

In one embodiment, the inherited condition comprises at least one genetically inherited mutation of at least one crucial gene, wherein said at least one mutation predisposes a person with this inherited condition to develop the disease phenotype. In another embodiment, the inherited condition is based on at least one genetically inherited polymorphism of at least one crucial gene, which predisposes a person with this condition to develop the disease phenotype. In this embodiment, the inherited condition may comprise the presence of a specific allelic variant of a crucial gene showing polymorphism. The specific allelic variant may predispose a person having said specific allelic variant for the development of the disease.

Examples of the inherited condition include, but are not limited to, predispositions leading to inherited immune or metabolic disorders, or to cancer development, some of which are depicted in table 1 below:

| Syndrome | Cloned Gene | Function | Chromosomal Location | Tumor Types |
|---|---|---|---|---|
| Li-Fraumeni Syndrome | p53 tumor suppressor | cell cycle regulation, apoptosis | 17p13 | brain tumors, sarcomas, leukemia, breast cancer |
| Familial Retinoblastoma | RB1 tumor suppressor | cell cycle regulation | 13q14 | retinoblastoma, osteogenic sarcoma |
| Wilms Tumor | WT1 tumor suppressor | transcriptional regulation | 11p13 | pediatric kidney cancer |
| Neurofibromatosis Type 1 | NF1 protein = neurofibromin 1 tumor suppressor | catalysis of RAS inactivation | 17q11.2 | neurofibromas, sarcomas, gliomas |
| Neurofibromatosis Type 2 | NF2 protein = merlin or neurofibromin 2 tumor suppressor | linkage of cell membrane to cytoskeleton | 22q12.2 | Schwann cell tumors, astrocytomas, meningiomas, ependynomas |
| Familial Adenomatous Polyposis | APC tumor suppressor | signaling through adhesion molecules to nucleus stabilization of beta-catenin | 5q21 | colon cancer |
| Tuberous sclerosis 1 | TSC1 protein = hamartin tumor suppressor | | 9q34 | facial angiofibromas |
| Tuberous sclerosis 2 | TSC2 protein = tuberin tumor suppressor | GTPase activation | 16 | benign growths (hamartomas) in many tissues, astrocytomas, rhabdomyosarcomas |
| Deleted in Pancreatic Carcinoma 4 | DPC4 also known as Smad4 tumor suppressor | regulation of TGF-β/BMP signal transduction | 18q21.1 | pancreatic carcinoma, colon cancer |
| Deleted in Colorectal Carcinoma | DCC tumor suppressor | transmembrane receptor involved in axonal guidance via netrins | 18q21.3 | colorectal cancer |

-continued

| Syndrome | Cloned Gene | Function | Chromosomal Location | Tumor Types |
| --- | --- | --- | --- | --- |
| Familial Breast Cancer | BRCA1 tumor suppressor | repair of double strand breaks by association with Rad51 protein | 17q21 | breast and ovarian cancer |
| Familial Breast Cancer | BRCA2 tumor suppressor | similar to BRCA1? | 13q12.3 | breast and ovarian cancer |
| Peutz-Jeghers Syndrome | STK11 tumor suppressor protein = serine-threonine kinase 11 | potential regulation of vascular endothelial growth factor (VEGF) pathway | 19p13.3 | hyperpigmentation, multiple hamartomatous polyps, colorectal, breast and ovarian cancers |
| Hereditary Nonpolyposis Colorectal Cancer type 1 HNPCC1 | MSH2 tumor suppressor | DNA mismatch repair | 2p22–p21 | colorectal cancer |
| Hereditary Nonpolyposis Colorectal Cancer type 2 HNPCC2 | MLH1 tumor suppressor | DNA mismatch repair | 3p21.3 | colorectal cancer |
| von Hippel-Lindau Syndrome | VHL tumor suppressor | regulation of transcription elongation | 3p26–p25 | renal cancers, hemangioblastomas, pheochromocytoma |
| Familial Melanoma | CDKN2A protein = cyclin-dependent kinase inhibitor 2A tumor suppressor | inhibits cell-cycle kinases CDK4 and CDK6 | 9p21 | melanoma, pancreatic cancer, others |
| Gorlin Syndrome: Nevoid basal cell carcinoma syndrome (NBCCS) | PTCH protein = patched tumor suppressor | transmembrane receptor for hedgehog signaling protein | 9q22.3 | basal cell skin cancer |
| Multiple Endocrine Neoplasia Type 1 | MEN1 tumor suppressor | unknown | 11q13 | parathyroid and pituitary adenomas, islet cell tumors, carcinoid |
| Multiple Endocrine Neoplasia Type 2 | RET, MEN2 | transmembrane receptor tyrosine kinase for glial-derived neurotrophic factor (GDNF) | 10q11.2 | medullary thyroid cancer, type 2A pheochromocytoma, mucosal hartoma |
| Beckwith-Wiedmann Syndrome | p57, KIP2 | cell cycle regulator | 11p15.5 | Wilms tumor, adrenocortical cancer, hepatoblastoma |
| Hereditary papillary renal cancer (HPRC) | MET | transmembrane receptor for hepatocyte growth factor (HGF) | 7q31 | renal papillary cancer |
| Cowden syndrome | PTEN tumor suppressor | phosphoinositide 3-phosphatase protein tyrosine phosphatase | 10q23.3 | breast cancer, thyroid cancer, head & neck squamous carcinomas |
| Hereditary prostate cancer numerous loci: HPC1(PRCA1), HPCX, MXI1, KAI1, PCAP | HPC1 and PRCA1 are same designation ribonuclease L (RNaseL) maps to this locus | RNaseL involved in mRNA degradation | 1q24–q25 | prostate cancer |
| Ataxia telangiectasia (AT) | ATM | DNA repair | 11q22.3 | lymphoma, cerebellar ataxia, immunodeficiency |
| Bloom syndrome | BLM | DNA helicase (?) | 15q26.1 | solid tumors, immunodeficiency |
| Xeroderma pigmentosum (XP) 7 complentation groups | XPA–XPG | DNA repair helicases, nucleotide excision repair | XPA = 9q22.3 XPC = 3p25 XPD = 19q13.2–q13.3 XPE = 11p12–p11 XPF = 16p13.3–p13.13 | skin cancer |
| Fanconi's anemia 8 complementation groups | FANCA–FANCH | components of DNA repair machinery | FANCA = 16q24.3 FANCC = 9q22.3 FANCD = 3p25.3 FANCE = 11p15 | acute myeloid leukemia (AML), pancytopenia, chromosomal instability |

Table 1: Hereditary predisposing disease conditions. [For further details on content of this table see: Online Mendelian Inheritance in Man, OMIM™. McKusick-Nathans Institute for Genetic Medicine, Johns Hopkins University (Baltimore, Md.) and National Center for Biotechnology Information, National Library of Medicine (Bethesda, Md.), 2000. World Wide Web URL: www.ncbi.nlm.nih.gov/omim/]

Furthermore, preclinical results indicate that 2PPA can be efficiently used as a therapeutic agent to treat and to suppress colorectal polyps in patients suffering from Familial Adenomatous Polyposis (FAP). Defined mutations in the APC/β-Catenin pathway genetically predispose patients carrying such mutations to develop FAP. Therefore, in a particularly preferred embodiment of the invention the inherited condition is FAP. The invention relates to the use of a histone deacetylase inhibitor for the manufacture of a medicament for the treatment or prevention of FAP. The invention further relates to the use of a histone deacetylase inhibitor for the manufacture of a medicament for the treatment or prevention of colon cancer wherein the medicament is administered to an individual suffering from FAP. The invention further relates to the use of a histone deacetylase inhibitor for the manufacture of a medicament for the treatment of individuals suffering from colon cancer and FAP.

In another embodiment of the invention, the inherited condition predisposes an individual to develop, e.g., an inflammatory disorder, including, but not limited, to Asthma, Atopic dermatitis, Psoriasis, Insulin-dependent Diabetes Mellitus, non-insulin-dependent Diabetes Mellitus, Graves disease, Autoimmune Polyendocrinopathy Syndrome, Inflammatory bowel disease, Inflammatory demyelinating polyneuropathy, Guillain-Barre-Syndrome, multiple and recurrent inflammatory fibroid polyps, neovascular inflammatory vitreoretinopathy, chronic neurologic cutaneous and articular syndrome, CINCA Syndrome, hereditary inflammatory vasculitis, familial recurrent arthritis autosomal dominant familial peroidic fever, familial cold autoinflammatory syndrome, Muckle-Wells syndrome, multiple sclerosis, hereditary myopathy, hereditary muscular dystrophy, Ankylosis Spondylitis, Bechterew Syndrome, Lupus Erythematosus and/or Osteomylitis.

Such diseases are linked to mutations or predisposing polymorphisms in genes selected from the group consisting of IL13, ALRH, BHR1, SCGB3A2, UGRP1, PLA2G7, PAFAH, PHF11, NYREN34, ATOD1, ATOD6, ATPD5, ATOD4, ATOD3 PSORS9, PSORS7, PSORS6, PSORS5, PSORS4, PSORS3, PSORS2, PSORS1, PSS1, IDDM1, TCF1, HNF1A, MODY3, Interferon production regulator factor (HNF1), albumin proximal factor, FOXP3, IPEX, AIID, XPID, PIDX Forkhead box P3 (scurfin), HLA, properdin factor B, glyoxalase-1, Kidd blood group, HLA-DQ (beta), GPD2, NEUROD1, NIDDM, CAPN10, Calpain-10, VEGF, MAPK8IP1, IB1, TCF1, HNF1A, MODY3, Interferon production regulator factor, albumin proximal factor, IPF1, IRS2, TCF2, HNF2, LF-B3, GCGR, HNF4A, TCF14, MODY1, NIDDM2, NIDDM3, Glut 2, Glut 4, GPD2, AIRE, APECED, IBD7, IBD9, IBD5, IBD3, IBD2, IBD4, IBD8, IBD6, CARD15, NOD2, ABCB1, DLG5, SLC22A4, SLC22A5, IBD1, CD, ACUG, NOD2, PMP22, GAS3, VRNI, D11S527, CIAS1, C1orf7, FCU, FCAS, AS, ANS, Major histocompatibility complex class I B, HLA-B27, FCGR3A, FCGR2A, CD16, IGFR3, TNFSF6, APT1LG1, FAS, FASL, TNFRSF1A, TNFA, PSTPIP1, PTPRC, CD45, TLA-A3, HLA-B7, HLA-Dw2, CRYAB, Immuneglobuline KM1/3, SLEB1, SLE1, PDCD1, SLEB2, SLEB3, SLEH1, SLEB4, DNASE1, SLEV1, SLEN1, SLEN2 and SLEN3.

In particular, the invention includes treatment of conditions and predisposing disorders which are linked to inherited genotypes, and wherein the development of the disorder is connected to a misguided regulation of cells of the immune system, e.g., due to misregulated expressions of inflammatory cytokines by these cells.

Cytokines are a diverse group of soluble proteins and peptides which act as regulators to modulate the functional activities of individual cells and tissues. They are designed to induce an inflammatory reaction as a defense against foreign or altered endogenous substances. In many respects the biological activities of cytokines resemble those of classical hormones produced in specialized glandular tissues by acting at a systemic level to induce biological phenomena such as inflammation, acute phase reaction and autoimmunity. However, inappropriate activation of inflammatory responses is the underlying cause of many common diseases and inflammatory reactions are, therefore, also an important target for drug development.

A number of cytokines accelerate inflammation and regulate a local or systemic inflammatory reaction either directly or through their ability to induce the synthesis of cellular adhesion molecules or other cytokines in certain cell types. The major cytokines that are responsible for early responses are IL1, IL6 and TNF-alpha. Other pro-inflammatory mediators include LIF, IFN-gamma, GM-CSF, IL11, IL12, IL18, and a variety of other chemokines.

However, the role of cytokines is not restricted to the inflammatory process alone, but have also a leading role in the development and propagation of autoimmune diseases. A classical example is rheumatoid arthritis where specific CD4+ T cells, most likely as a response to an unknown exogenous or endogenous antigen, induce an immune response in affected joints (Olsen et al., 2003, New England Journal of Medicine 350, 2167-79). Consequently, recruited monocytes, macrophages, and fibroblasts produce cytokines such as tumor necrosis factor-α (TNF-α) and interleukin-1 within the synovial cavity. These cytokines are central to a damaging cascade, ultimately triggering the production of matrix metalloproteinases and osteoclasts, which results in irreversible damage to soft tissues and bones.

TNF-α, an inflammatory cytokine that is released by activated monocytes, macrophages, and T lymphocytes, promotes inflammatory responses that are important in the pathogenesis of rheumatoid arthritis. Patients with rheumatoid arthritis have high concentrations of TNF-α in the synovial fluid. TNF-α is localized to the junction of the inflammatory pannus and healthy cartilage, and high synovial fluid TNF-α concentrations are associated with the erosion of bone.

Not surprisingly, TNF antagonists appear to be among the most effective treatments available for rheumatoid arthritis. The response is generally rapid, often occurring within a few weeks, although not all patients have a response.

Agents directed against TNF-α are not only effective in the treatment of chronic autoimmune disorders such as rheumatoid arthritis, but also in the treatment of Chrohn's disease, ulcerative colitis, Sjögren's syndrome, scleroderma, psoriatic arthritis, ankylosing spondylitis, refractory uveitis, Behcet's disease, adult-onset Still's disease, and Wegener's granulomatosis.

Another example is psoriasis, where a T cell mediated immune response is directed against keratinocytes. These T lymphocytes encounter the initiating antigen in the dermis or epidermis, and secrete type-1 cytokines (Th1), particularly interferon-γ, interleukin 2, and TNF-α. These secretions result in proliferation and decreased maturation of keratinocytes and associated vascular changes. Secretion of other cytokines such as interleukin 8 contribute to the complete picture of psoriasis (Lebwohl, 2004, The Lancet 361, 1197-1204).

Further evidence for the causal involvement of cytokines in autoimmune diseases has come from observations made after the use of cytokines in the treatment of various diseases (Krause et al., 2003, The American Journal of Medicine 115, 390-397). Interestingly, they are associated with side effects such as the triggering and exacerbation of immune and autoimmune conditions, which may evolve into overt autoimmune disorders. These autoimmune manifestations seem to be more common in patients with a pre-existing tendency towards autoimmunity.

Exacerbation of multiple sclerosis has been observed during treatment with interferon-γ. The frequency of autoimmune manifestations associated with interferon-γ therapy seems to be low but there have been reports of systemic lupus erythematosus in patients treated with interferon-γ alone, as well as in combination with interferon-γ for myeloproliferative disorders. Interferon-γ is involved in the pathogenesis of systemic lupus erythematosus in animal models. Administration of interferon-γ accelerates the rate of progression to glomerulonephritis in lupus-prone (NZBXNZW)F1 mice, which is prevented by treatment with anti-interferon-γ antibodies. Elevated serum levels of interferon-γ have been reported in patients with systemic lupus erythematosus. Interferon-γ is produced by natural killer cells and binds to the type II interferon receptor. It is less effective than interferon-γ in activating natural killer cells and has less potent antiviral and antitumor effects. However, interferon-γ is the most potent inducer of macrophage activation and major histocompatibility class II molecules. It stimulates immunoglobulin secretion by B cells and promotes T-cell differentiation towards the T helper 1 type.

Interleukin 2 is secreted by activated T cells with antitumor activity. It is effective in the treatment of metastatic malignant melanoma and renal cell carcinoma. It induces T-cell proliferation, potentiates B-cell growth, and enhances natural killer cell and monocyte activation. The most common autoimmune side effect seen under interleukin 2 therapy is immune-mediated thyroid disease. Reversible thyroid dysfunction occurs frequently in patients with cancer who are treated with interleukin either alone or in conjunction with lymphokine-activated killer cells or interferon-γ. In a study with interleukin 2 in patients with metastatic renal cell carcinoma, antithyroid antibodies were detected in 18% (60/329) of patients. Other much less common phenomena that may be considered autoimmune have been described in association with interleukin 2 therapy. These include rheumatoid arthritis, psoriatic arthropathy, ankylosing spondylitis, and Reiter's syndrome. The triggering of arthritis may be explained by induction of autoantigen recognition by T cells infiltrating the joints, leading to inflammation. Interleukin 2 may potentiate a breakdown of immunologic tolerance to muscle-specific and tumor antigens, resulting in destruction of both tumor and muscle cells. One patient with metastatic renal cell carcinoma treated with interleukin 2 and lymphokine-activated killer cells developed an acute exacerbation of systemic sclerosis. Serum levels of interleukin 2 and soluble interleukin 2 receptor are elevated in patients with systemic sclerosis and correlate with disease duration and activity. These observations may explain the association between interleukin 2 therapy and the development of systemic sclerosis.

For further details on the diseases described in the following section, see also: Online Mendelian Inheritance in Man, OMIM™. McKusick-Nathans Institute for Genetic Medicine, Johns Hopkins University (Baltimore, Md.) and National Center for Biotechnology Information, National Library of Medicine (Bethesda, Md.), 2000 [World Wide Web URL: www.ncbi.nlm.nih.gov/omim/].

Asthma

Genes/gene map loci involved in inheritance of this condition:

Gene map locus 13q14.1, 7p15-p14, 6p21.2-p12, 5q31-q34, 5q31-q33, 5q31 (www.ncbi.nlm.nih.gov/Omim/getmap.cgi?1600807)

IL13, ALRH Interleukin-13, BHR1 Bronchial hyperresponsiveness-1 (bronchial asthma), SCGB3A2 (Secretoglobin, family 3A, member 2), UGRP1 (uteroglobin-related protein 1), PLA2G7 (Phospholipase A2, group VII), PAFAH (platelet-activating factor acetylhydrolase), PHF11, NYREN34 PHD finger protein 11

Bronchial asthma is the most common chronic disease affecting children and young adults. It is a complex genetic disorder with a heterogeneous phenotype, largely attributed to the interactions among many genes and between these genes and the environment.

Longo et al. (1987, Am. J. Dis. Child. 141, 331-334) postulated that asthma can be inherited as a mendelian dominant (with variable penetrance); Townley et al. (1986, J. Allergy Clin. Immun. 77: 101-107) supported polygenic inheritance. Longo et al. (1987, Am. J. Dis. Child. 141, 331-334) found that among the healthy parents of asthmatic children, tests of airway responsiveness to carbachol showed a bimodal distribution of responsiveness; in 85% of couples who had an asthmatic child, one or both parents had normal airway responsiveness consistent with autosomal an dominant trait.

The new occurrence of such diseases after organ transplantation suggests that genetic predisposition may be confined to the particular organs or physiologic systems. A new occurrence of asthma after bone marrow transplantation from a donor who had asthma (Agosti et al., 1998, New Eng. J. Med. 319, 1623-1628) or new asthma in a recipient who had lungs transplanted from an asthmatic donor (Corris et al., 1993, Lancet 341, 1369-1371) suggests that expression of some inflammatory disorders is a result of both systemic (often immune) influence and end-organ specificity, each under distinct genetic control.

Atopic Dermatitis

Genes/gene map loci involved in inheritance of this condition:

Gene map locus 20p, 17q25, 13q12-q14, 5q31-q33, 3q21 (www.ncbi.nlm.nih.gov/Omim/getmap.cgi?1603165)

ATOD1 (Dermatitis, atopic, 1), ATOD6 (Dermatitis, atopic, 6), ATPD5 (Dermatitis, atopic, 5), ATOD4 (Dermatitis, atopic, 4), ATOD3 (Dermatitis, atopic, 3)

Many inflammatory diseases, such as atopic eczema, are genetically complex, with multiple alleles at several loci thought to be involved in their pathogenesis.

In developed countries, the prevalence of atopic dermatitis is said to be approximately 15%, with a steady increase during the end of the 20th century (Kay et al., 1994, J. Am. Acad. Derm. 30, 35-39; Taylor et al., 1984, Lancet 2, 1255-1259). To identify susceptibility loci for atopic dermatitis, Lee et al. (2000, Nature Genet. 26, 470-473) ascertained 199 families with at least 2 affected sibs based on established diagnostic criteria. A genomewide linkage study revealed highly significant evidence for linkage on 3q21 at marker D3S3606. Moreover, this locus provides significant evidence for linkage of allergic sensitization under the assumption of paternal imprinting, further supporting the presence of an atopy gene in this region.

Atopic dermatitis (ATOD), also known as eczema, commonly begins in infancy and early childhood, and is typified by itchy inflamed skin. It affects 10 to 20% of children in western societies and shows a strong familial aggregation. Eighty percent of cases of ATOD have elevations of the total serum IgE concentration. Cookson et al. (2001, Nature Genet. 27, 372-373) examined 148 nuclear families recruited through children with active ATOD. The families contained 383 children and 213 sib pairs; 254 children had physician-diagnosed ATOD, 153 had asthma, and 139 had both. Children with ATOD were aged 6.9+/−4.4 years, and 124 were male. The age of onset of disease was less than 2 years in 90% of children. Cookson et al. (2001, Nature Genet. 27, 372-373) found that 51.5% of children had moderate disease and 28.6% had severe disease. The serum IgE concentration was much higher in children with ATOD and asthma together than in children with asthma alone or with ATOD alone. Using 385 microsatellite markers they identified linkage to ATOD on chromosome 1q21 (ATOD2; 605803) and 17q25 (ATOD4; 605805), and linkage to asthma on 20p (see ATOD3, 605804). Linkage of chromosome 20p to children with both ATOD and asthma was not greatly different than that to children with asthma alone, indicating that the combination of ATOD and asthma may correspond to a genetic subtype of disease. The total serum IgE concentration was linked to chromosome 16q-tel. Cookson et al. (2001, Nature Genet. 27, 372-373) conclude that their results indicated that several genes influence ATOD.

Psoriasis

Genes/gene map loci involved in inheritance of this condition:

Gene map locus 19p13, 17q25, 1q21, 1p, 6p21.3, 4q31-q34, 4q, 3q21

(www.ncbi.nlm.nih.gov/Omim/getmap.cgi?1177900)

PSORS7 (Psoriasis susceptibility 7), PSORS4 (Psoriasis susceptibility 4), PSORS5 (Psoriasis susceptibility 5), PSORS3 (Psoriasis susceptibility 3), PSORS9 (Psoraisis susceptibility 9), PSORS1 (Psoriasis susceptibility 1), PSORS2, PSS1 (Psoriasis susceptibility 2), PSORS6 (Psoriasis susceptibility 6)

Several psoriasis susceptibility loci have been mapped: PSORS1 on 6p21.3, PSORS2 on 17q, PSORS3 on 4q, PSORS4 on 1cen-q21, PSORS5 on 3q21, PSORS6 on 19p, PSORS7 on 1p, and PSORS9 on 4q31. The loci on 6p and 17q appear to be well established. Additional putative psoriasis candidate loci have been reported on 16q and 20p) (Nair et al., 1997, Hum. Molec. Genet. 6, 1349-1356).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis. The usual age of onset of psoriasis is between 15 and 30 years, although it can be present at any age.

From studies in a 'skin equivalent model,' Saiag et al. (1985, Science 230, 669-672) concluded that the primary defect in psoriasis may reside in the dermal fibroblasts. Psoriatic fibroblasts could induce hyperproliferative activity in normal keratinocytes. The high rate of proliferation of psoriatic epidermis could not be suppressed by normal fibroblasts though.

The multifactorial etiology of psoriasis is well established. Although environmental factors, such as streptococcal infections, affect the onset of the disease, family studies indicate a strong genetic component. Twin studies show the concordance in monozygotic twins to be 65 to 70% (Brandrup et al., 1982, Acta. Derm. 62, 229-236; Farber et al., 1974, Arch. Derm. 109, 207-211), compared to 15 to 20% in dizygotic twins. Family studies estimate the risk to first-degree relatives at between 8 to 23%.

Diabetes, Insulin-Dependent Diabetes Mellitus (IDDM1)

Genes/gene map loci involved in inheritance of this condition:

Gene map locus Xp11.23-q13.3, 12q24.2, 6p21.3

(www.ncbi.nlm.nih.gov/Omim/getmap.cgi?1222100)

IDDM1 Insulin-dependent diabetes mellitus-1, TCF1, HNF1A, MODY3, FOXP3, IPEX, AIID, XPID, PIDX Forkhead box P3 (scurfin), HLA, properdin factor B, glyoxalase-1, Kidd blood group, HLA-DQ(beta)

The type of diabetes mellitus called IDDM is a disorder of glucose homeostasis that is characterized by susceptibility to ketoacidosis in the absence of insulin therapy. It is a genetically heterogeneous autoimmune disease affecting about 0.3% of Caucasian populations (Todd, 1990, Immun. Today 11, 122-129). Genetic studies of IDDM have focused on the identification of loci associated with increased susceptibility to this multifactorial phenotype.

IDDM exhibits 30 to 50% concordance in monozygotic twins, suggesting that the disorder is dependent on environmental factors as well as genes. The average risk to sibs is 6%) (Todd et al., 1990, Immun. Today 11, 122-129). Recessive, dominant, and multifactorial hypotheses have been advanced, as well as 'susceptibility' hypotheses (Rotter et al., 1981, Am. J. Hum. Genet. 33, 835-851). Genetic and environmental influences in IDDM were reviewed by Craighead (1978, New Eng. J. Med. 299, 1439-1445). Usually in a genetic disease the most severe form of a disorder shows the clearest genetic basis. It is therefore surprising to find that the genetics of IDDM is less clear than that of NIDDM (noninsulin-dependent diabetis mellitus). Concordance in NIDDM was 100% for identical twins in which the index case had onset of diabetes after age 45 years, and nearly half had a diabetic parent, while discordance was found in half the pairs with earlier onset, few of whom had a family history of diabetes (Tattersall and Pyke, 1972, Lancet II, 1120-1125).

Clerget-Darpoux et al. (1981, Ann. Hum. Genet. 45, 199-206) concluded that the data in 30 multiplex families best fitted a model with a susceptibility gene which was not linked to but interacted with the HLA system. Under 3 different genetic models for IDDM, Hodge et al. (1981, Lancet II, 893-895) found evidence for linkage with 2 different sets of marker loci: HLA, properdin factor B, and glyoxalase-1 on chromosome 6, and Kidd blood group (then thought to be on chromosome 2, but later shown to be on chromosome 18). Thus, 2 distinct disease-susceptibility loci may be involved in IDDM, a situation also postulated for Graves disease.

IDDM, although called the juvenile-onset type of diabetes, has its onset after the age of 20 years in 50% of cases. Caillat-Zucman et al. (1992, J. Clin. Invest. 90, 2242-2250) investigated whether the association of IDDM with certain HLA alleles, well documented in pediatric patients, also holds for adults. Interestingly, they found quite different HLA class II gene profiles, with a significantly higher percentage of non-DR3/non-DR4 genotypes and a lower percentage of DR3/4 genotypes in older patients. Although the non-DR3/non-DR4 patients presented clinically as IDDM, they showed a lower frequency of islet cell antibodies (ICA) at diagnosis and a significantly milder insulin deficiency. These data (1) suggest these subjects probably represent a particular subset of IDDM patients in whom frequency increases with age; and (2) confirm the genetic heterogeneity of IDDM.

Todd et al. (1987, Nature 329, 599-604) estimated that more than half of the inherited predisposition to IDDM maps to the region of the HLA class II genes on chromosome 6. Analysis of the DNA sequences from diabetics indicated that alleles of HLA-DQ(beta) determined both disease susceptibility and resistance. A non-asp at residue 57 of the beta-chain in particular confers susceptibility to IDDM and the autoimmune response against the insulin-producing islet cells. Morel et al. (1988, Proc. Nat. Acad. Sci. 85, 8111-8115) found that HLA haplotypes carrying an asp in position 57 of the DQ-beta chain were significantly increased in frequency among nondiabetics, while non-asp57 haplotypes were significantly increased in frequency among diabetics. Ninety-six percent of the diabetic probands were homozygous non-asp/non-asp as compared to 19.5% of healthy, unrelated controls. This represented a relative risk of 107 for non-asp57 homozygous individuals.

Diabetes Mellitus, Type II Noninsulin-Dependent Diabetes Mellitus Maturity-Onset Diabetes (NIDDM)

Genes/gene map loci involved in inheritance of this condition:

Gene map locus 20q22-q13.1, 20q12-q13.1, 17q25, 17cen-q21.3, 13q34, 13q12.1, 12q24.2, 11p12-p11.2, 6p12, 2q37.3, 2q32, 2q24.1

(www.ncbi.nlm.nih.gov/Omim/getmap.cgi?1125853)

GPD2 (Glycerol-3-phosphate dehydrogenase 2, mitochondrial), NEUROD1, NIDDM (Neurogenic differentiation 1), CAPN10 (Calpain-10), VEGF (Vascular endothelial growth factor), MAPK8IP1 (Mitogen-activated protein kinase 8-interacting protein 1), IB1, TCF1, HNF1A, MODY3, albumin proximal factor, IPF1 (Insulin promoter factor 1), IRS2 (Insulin receptor substrate 2), TCF2, HNF2, LF-B3, GCGR (Glucagon receptor), HNF4A, TCF14, MODY1, NIDDM2, NIDDM3 (Noninsulin-dependent diabetes mellitus 2 and 3), Glut 2, Glut 4

There is evidence that more than one gene locus is involved in the causation of noninsulin-dependent diabetes mellitus (NIDDM). One form of NIDDM linked to 2q may be caused by mutation in the gene encoding calpain-10 (CAPN10), another on chromosome 12q, NIDDM2, was found in a Finnish population, and another locus was identified on chromosome 20, NIDDM3. A mutation has been observed in hepatocyte nuclear factor-4-alpha (HNF4A) in a French family with NIDDM of late onset. Mutations in the NEUROD1 gene on chromosome 2q32 were found to cause type II diabetes mellitus in 2 families. Mutation in the GLUT4 glucose transporter was associated with NIDDM in one patient and in the GLUT2 glucose transporter in another. Mutation in the MAPK81P1 gene, which encodes the islet-brain-1 (IB1) protein, was found in a family with type II diabetes in individuals in 4 successive generations. In French white families, Vionnet et al. (2000, Am. J. Hum. Genet. 67, 1470-1480) found evidence for a susceptibility locus for type II diabetes on 3q27-qter. They confirmed the diabetes susceptibility locus on 1q21-q24 reported by Elbein et al. (1999, Diabetes 48, 1175-1182) in whites and by Hanson et al. (1998, Am. J. Hum. Genet. 63, 1130-1138) in Pima Indians. A mutation in the GPD2 gene on chromosome 2q24.1, encoding mitochondrial glycerophosphate dehydrogenase, was found in a patient with type II diabetes mellitus and in his glucose-intolerant half-sister. Triggs-Raine et al. (2002, Proc. Nat. Acad. Sci. 99, 4614-4619) stated that in the Oji-Cree, a gly319-to-ser change in HNF1-alpha behaves as a susceptibility allele for type II diabetes. Mutation in the HNF1B gene was found in 2 Japanese patients with typical late-onset type II diabetes. Mutations in the IRS1 gene have been found in patients with type II diabetes. Reynisdottir et al. (2003, Am. J. Hum. Genet. 73, 323-335) mapped a susceptibility locus for type II diabetes to chromosome 5q34-q35.2

Multiple Sclerosis

Genes/gene map loci involved in inheritance of this condition:

Gene map locus 1q31-q32

(www.ncbi.nlm.nih.gov/entrez/dispomim.cgi?id=126200)

PTPRC/CD45, HLA-A3, HLA-B7, HLA-Dw2

A point mutation in the PTPRC gene, also known as CD45, is associated with the development of multiple sclerosis. An association with the HLA-DRB1*1501-DQB1*0602 haplotype has been repeatedly demonstrated in high-risk (northern European) populations. Associations with HLA-A3, HLA-B7, and HLA-Dw2 have been demonstrated also. The association with Dw2 seems to be especially strong and probably indicates an immune-response mechanism.

Steinman (1996, Cell 85, 299-302) reviewed what was known about the molecular mechanisms in the pathogenesis of multiple sclerosis, the most common autoimmune disease involving the nervous system due to an immunologic attack on myelin. It is estimated that in the United States approximately 250,000 individuals suffer from MS. The concordance rate among monozygotic twins is 30%, a 10-fold increase over that in dizygotic twins or first-degree relatives.

The proteins of the myelin sheath were separated by van Noort et al. (1995, Nature 375, 798-801) using reversed-phase HPLC and discovered that a particular fraction in the myelin of MS brain, but not in the myelin taken from healthy brain, stimulated proliferation of T cells. They showed that alpha-crystallin B (CRYAB) is expressed in glial cells from MS lesions but not in white matter from healthy individuals or in unaffected white matter from MS brain. This small heat-shock protein was found in oligodendroglial cells as well as in astrocytes in plaques from patients with acute and chronic MS. Progressive oligodendrocyte loss is part of the pathogenesis of MS. Oligodendrocytes are vulnerable to a variety of mediators of cell death, including free radicals, proteases, inflammatory cytokines, and glutamate excitotoxicity. Proinflammatory cytokine release in MS is mediated in part by microglial activation.

Autoimmune Polyendocrinopathy Syndrome, Type I

Genes/gene map loci involved in inheritance of this condition:

Gene map locus 21q22.3

(www.ncbi.nlm.nih.gov/Omim/getmap.cgi?1240300)

AIRE, APECED

Autoimmune polyendocrinopathy syndrome type I is caused by a mutation in the autoimmune regulator gene (AIRE) and is characterized by the presence of 2 of 3 major clinical symptoms: Addison disease, and/or hypoparathyroidism, and/or chronic mucocutaneous candidiasis.

Foz et al. (1970, Lancet II, 269 only) made a brief note of a sibship, offspring of first-cousin parents, containing 2 female sibs with idiopathic Addison disease. One also had primary hypoparathyroidism and one had oral candidiasis. Ahonen (1985, Clin. Genet. 27, 535-542) provided a genetic analysis of 58 patients in 42 families and corroborated autosomal recessive inheritance. Cetani et al. (2001, J. Clin. Endocr. Metab. 86, 4747-4752) identified an Italian family with autoimmune polyendocrinopathy syndrome and a pattern of inheritance suggestive of a dominant mechanism.

Blizzard and Kyle (1963, J. Clin. Invest. 42, 1653-1660) offered the first substantial evidence for the autoimmune concept. They found antiadrenal antibodies in 36 of 71 patients with Addison disease and antithyroid antibodies in 22. Hung et al. (1963, New Eng. J. Med. 269, 658-663) found circulating adrenal antibodies in 2 sibs with Addison disease. A third sib had died from Addison disease. One of the affected sibs also had hypoparathyroidism, pernicious anemia, and superficial moniliasis.

In studies performed in Finland and Estonia, Krohn et al. (1992, Lancet 339, 770-773) screened serum samples from patients with Addison disease as part of the type I polyendocrine autoimmunity syndrome. In 3 patients they demonstrated precipitating antibodies against adrenal proteins. They cloned these proteins and found that one of them was 17-alpha-hydroxylase, the steroid hormone that is deficient or defective in one form of congenital adrenal hypoplasia. Patients with idiopathic Addison disease likewise showed antibodies to this protein.

Chrohn's disease—Inflammatory bowel disease (IBD)

Genes/gene map loci involved in inheritance of this condition:

Gene map locus 19p13, 16q12, 16p, 14q11-q12, 12p13.2-q24.1, 6p, 5q31, 3p26, 1p36

(www.ncbi.nlm.nih.gov/Omim/getmap.cgi?1266600)

IBD7 (Inflammatory bowel disease-7), IBD9 (Inflammatory bowel disease 9), IBD5 (Inflammatory bowel disease-5), IBD3 (Inflammatory bowel disease-3), IBD2 (Inflammatory bowel disease-2), IBD4 (Inflammatory bowel disease-4), IBD8 (Inflammatory bowel disease-8), IBD6 (Inflammatory bowel disease-6), CARD15 (Caspase recruitment domain family, member 15), NOD2, IBD1, CD (Celiac disease; HLA-DQ2/8), ACUG, PSORAS1, ABCB1, DLG5, SLC22A4, SLC22A5.

There is evidence that mutations in the CARD15 gene are associated with susceptibility to Crohn disease in families linked to chromosome 16. An allele of the ABCB1 gene is associated with susceptibility to Crohn disease. Other loci for IBD include IBD2 on 12p13.2-q24.1, IBD3 on 6p, IBD4 on 14q11-q12, IBD5 on 5q31, IBD6 on 19p13, IBD7 on 1p36, and IBD8 on 16p not linked to CARD15. Polymorphism in the DLG5 gene, which maps to 10q23, is associated with the risk of developing IBD; genetic interaction studies suggested interactions between the 113A variant of the DLG5 gene and risk-associated CARD15 alleles. A haplotype defined by a missense substitution in SLC22A4 and a G-to-C transversion in the SLC22A5 promoter is associated with susceptibility to Crohn disease.

Inflammatory bowel disease is characterized by a chronic relapsing intestinal inflammation. IBD is subdivided into Crohn disease and ulcerative colitis phenotypes. Crohn disease and ulcerative colitis have a combined prevalence of 200 to 300 per 100,000 in the United States. Crohn disease may involve any part of the gastrointestinal tract, but most frequently the terminal ileum and colon. Bowel inflammation is transmural and discontinuous; it may contain granulomas or be associated with intestinal or perianal fistulas. In contrast, in ulcerative colitis, the inflammation is continuous and limited to rectal and colonic mucosal layers; fistulas and granulomas are not observed. In approximately 10% of cases confined to the rectum and colon, definitive classification of Crohn disease or ulcerative colitis cannot be made and are designated 'indeterminate colitis.' Both diseases include extraintestinal inflammation of the skin, eyes, or joints.

Crohn disease and ulcerative colitis are commonly classified as autoimmune diseases. The prevalence of inflammatory bowel disease is increased in individuals with other autoimmune diseases, particularly ankylosing spondylitis, psoriasis, sclerosing cholangitis, and multiple sclerosis. There is strong evidence from twin studies, familial risk data, and segregation analysis that inflammatory bowel disease, especially Crohn disease, is genetic; (Yang and Rotter, 1994, Baltimore: Williams and Wilkins, 32-64; (Duerr, 1996, Inflam. Bowel Dis. 2, 48-60). Crohn disease and ulcerative colitis are considered complex genetic traits as inheritance does not follow any simple mendelian models. IBD has been linked to chromosomes 16p12-q13 (IBD1), 12p13 (IBD2), and 6p (IBD3).

Inflammatory demyelinating Polyneuropathy—Guillain-Barre-Syndrome

Genes/gene map loci involved in inheritance of this condition:

There is evidence that some cases of inflammatory demyelinating polyneuropathy may be caused by mutation in the PMP22 gene (PERIPHERAL MYELIN PROTEIN 22, alternative titles: GROWTH ARREST-SPECIFIC 3; GAS3) on chromosome 17.

(www.ncbi.nlm.nih.gov/entrez/dispomim.cgi?id=601097)

Inflammatory demyelinating polyneuropathy, a putative autoimmune disorder presenting in an acute (Guillain-Barre syndrome) or a chronic form, has also been reported as familial (Wilmsechurst et al., 1999, Europ. J. Neurol. 6, 499-503). Occurrence in first-degree relatives is rare; (Saunders and Rake, 1965, Lancet 2, 1106-1107; MacGregor, 1965, Lancet 2, 1296 ; Davidson et al., 1992, J. Neurol. Neurosurg. Psychiat. 55, 508-509) reported the disorder in a father and son. The father's illness was at the age of 58 years. He recovered completely after a 2-month hospitalization during which he was treated with plasmapheresis. The son was hospitalized at the age of 43 years; he also was treated with plasmapheresis, with complete recovery in 3 months. Davidson et al. (1992, J. Neurol. Neurosurg. Psychiat. 55, 508-509) commented on remarkably similar HLA typing results in the father and son.

Guillain-Barre syndrome has been associated with antecedent Campylobacter jejuni infections. Ma et al. (1998, Ann. Neurol. 44, 815-818) found a higher frequency of a rare TNFA polymorphism (-308G-A) in 43 Japanese Guillain-Barre patients who had had antecedent infection with Campylobacter jejuni than in 85 community controls.

Despite the association of Guillain-Barre syndrome with antecedent Campylobacter jejuni infection, only a minority of the infected individuals develop the disease, implying a role for genetic factors in conferring susceptibility. Pandey and Vedeler (2003, Neurogenetics 4, 147-149) genotyped 83 patients and 196 healthy controls in Norway for immunoglobulin KM genes (genetic markers of the constant region of kappa immunoglobulin chains) by PCR-RFLP. The frequency of KM3 homozygotes was significantly increased in the patients compared with controls. Conversely, the frequency of KM1/KM3 heterozygotes was significantly decreased in patients compared with controls. The results suggested that KM genes may be relevant to the etiology of Guillain-Barre syndrome.

Multiple and Recurrent Inflammatory Fibroid Polyps

Anthony et al. (1984, Gut 25, 854-862) reported a family from Devon, England, in which a female in each of 3 successive generations had multiple inflammatory fibroid polyps. The grandmother had had 9 polyps resected over 11 years; the mother, 7 over 18 years; and the daughter, 6 over 6 years. Characteristically, inflammatory fibroid polyps are solitary tumors in the stomach which consist of loosely organized, vascular and fibrous tissue with a variable number of eosinophils. Recurrence or familial occurrence had not been previously encountered. Conventional histology, electron microscopy, and immunohistology suggested to Anthony et al. (1984, Gut 25, 854-862) that the lesion is a self-limiting proliferation of histiocytes. The initiating event or stimulus remains unknown. None of the patients or their relatives were known to have allergies, dietary fads, or gastrointestinal infections. The grandmother's polyps were removed from the ileum and gastric antrum; in the other 2 patients, they were removed from the ileum, where they had caused intussusception.

Neovascular Inflammatory Vitreoretinopathy

Genes/gene map loci involved in inheritance of this condition:

Gene map locus 11q13

(www.ncbi.nlm.nih.gov/Omim/getmap.cgi?1193235)

VRNI, D11S527

Autosomal dominant neovascular inflammatory vitreoretinopathy is a blinding disorder that shares some clinical features with retinitis pigmentosa, uveitis, and proliferative diabetic retinopathy. Features include prominent ocular inflammation; vascular dropout, large spots of hyperpigmentation, and neovascularization of the peripheral and posterior retina; vitreous hemorrhage; and retinal detachment. Sheffield et al. (1992, Am. J. Hum. Genet. 51 (suppl.), A35) established close linkage to markers that map to 11q13. In a single large pedigree, linkage analysis with the closest marker, D11S527, demonstrated a maximum lod of 6.29 with no recombinants. Stone et al. (1992, Hum. Molec. Genet. 1, 685-689) reported that they had found 34 affected members in this pedigree, that no recombinants were found between the disease phenotype and D11S527, and that multipoint analysis yielded a maximum lod score of 11.9 centered on this marker. Another inherited retinal dystrophy, Best disease (VMD2), also maps to 11q13. However, Sheffield et al. (1992, Am. J. Hum. Genet. 51 (suppl.), A35) stated that the 2 diseases appear to be at least 10 cM apart. Furthermore, Sheffield considered it unlikely that VRNI is allelic to familial exudative vitreoretinopathy (EVR1). First, the 2 disorders are clinically distinct. For example, vitreous cells are present in VRNI and not in EVR1. On electrooculography, VRNI has a distinct b-wave abnormality, whereas the b-wave is normal in EVR1. Second, whereas EVR1 maps about 7 cM from marker D11S527, no recombination has been found between VRNI and D11S527. There may be a clustering of genes in the proximal portion of 11q that have a common function and owe their proximity to a common ancestry.

Chronic neurologic cutaneous+articular syndrome (CINCA Syndrome)

Genes/gene map loci involved in inheritance of this condition:

Gene map locus 1q44
(www.ncbi.nlm.nih.gov/Omim/getmap.cgi?1607115)
CIAS1, C1orf7, FCU, FCAS The CINCA syndrome can be caused by mutation in the cryopyrin gene (CIAS1). Chronic infantile neurologic cutaneous and articular (CINCA) syndrome is a severe chronic inflammatory disease of early onset, characterized by cutaneous symptoms, central nervous system involvement, and arthropathy (Feldmann, 2002, Am. J. Hum. Genet. 71, 198-203).

Feldmann et al. (2002, Am. J. Hum. Genet. 71, 198-203) identified heterozygous missense mutations in exon 3 of the CIAS1 gene in the affected members of each of 7 families with CINCA syndrome.

Of 3 patients with CINCA syndrome studied by Leone et al. (2003, Europ. J. Pediat. 162, 669-673), only 1 had a mutation in exon 3 of the CIAS1 gene. Aksentijevich et al. (2002, Arthritis Rheum. 46, 3340-3348) identified heterozygous missense mutations in exon 3 of the CIAS1 gene in 6 of 13 patients with CINCA syndrome. No mutation in the CIAS1 gene was found in the other 7 patients, suggesting genetic heterogeneity. Aksentijevich et al. (2002, Arthritis Rheum. 46, 3340-3348) found no discernible differences in the clinical features of patients with or without mutations in CIAS1.

Hereditary Inflammatory Vasculitis

This condition was described by Reed et al. (1972, Brit. J. Derm. 87, 299-307) in 3 generations of a family. Lesions were of two types: 1) multiple small to medium-sized nodules on the arms, legs and buttocks and 2) multiple larger, firm nodules, resembling rheumatoid nodules, over bony prominences. The lesions were present from birth or early life. Exposure to sunlight aggravated the lesions, whereas chloroquine suppressed them completely. Histology showed lymphocytic vasculitis without necrosis, extending deep into the fat. A relationship to lupus erythematosus (LE) was postulated. 'Rheumatoid arthritis' and discoid LE were present in the family. No male-to-male transmission was observed Familial Recurrent Arthritis Genes/gene map loci involved in inheritance of this condition:

Gene map locus 15q24-q26.1, 15q24-q25.1
(www.ncbi.nlm.nih.gov/entrez/dispomim.
cgi?id=604416)
PSTPIP1

This disorder is caused by mutations in the PSTPIP1 gene. Yeon et al. (2000, Am. J. Hum. Genet. 66, 1443-1448) used linkage mapping to locate the PAPAS gene on chromosome 15q (maximum 2-point lod score of 5.83 with recombination fraction=0 at D15S206). Under the assumption of complete penetrance, haplotype analysis of recombination events defined a disease interval of 10 cM between D15S1023 and D15S979. They indicated that the gene is in the same region as the IL16 gene and the CRABP1 gene (incorrectly stated to be the CRABP2 gene), which map to 15q26.1 and 15q24, respectively.

Lindor et al. (1997, Mayo Clin. Proc. 72, 611-615) described a multigeneration family with transmission of an autosomal dominant disorder characterized by pyogenic arthritis, pyoderma gangrenosum, and severe cystic acne. Ten affected family members manifested variable expression of pauciarticular, nonaxial, destructive, corticosteroid-responsive arthritis that began in childhood; pyoderma gangrenosum; and severe cystic acne in adolescence and beyond. Other less commonly associated features included adult-onset insulin-dependent diabetes mellitus, proteinuria, abscess formation at the site of parenteral injections, and cytopenias attributable to sulfonamide medications.

Peroidic fever, familial, autosomal dominant

Genes/gene map loci involved in inheritance of this condition:

TNFRSF1A

Autosomal dominant periodic fever is caused by mutations in the tumor necrosis factor receptor-1 gene (TNFRSF1A). McDermott et al. (I999, Cell 97, 1-20) identified germline mutations in the TNFRSF1A gene, which had been identified as a candidate gene by linkage studies. The families studied included those reported by Mulley et al. (1998, Am. J. Hum. Genet. 62, 884-889) and McDermott et al. (1998, Am. J. Hum. Genet. 62, 1446-1451), a Finnish family reported by Karenko et al. (I992, J. Int. Med. 232, 365-369), and 3 small North American families of Irish/English/German, Irish, and French-Canadian ancestry.

Toro et al. (2000, Arch. Derm. 136, 1487-1494) described the cutaneous features of 25 patients with clinically and molecularly diagnosed FPF, which they referred to as 'tumor necrosis factor receptor-associated periodic syndrome' (TRAPS). Twenty-one patients (84%) had cutaneous manifestations. Migratory macules and patches were the most common findings. In addition, 10 patients (40%) exhibited erythematous edematous plaques. Lesions usually occurred during febrile episodes, were most commonly seen on the extremities, were often associated with myalgia, and lasted 4 to 21 days. Biopsies of lesional skin were obtained from 10 patients. The histologic findings were nonspecific, consisting of infiltrating T lymphocytes and monocytes, and could not be distinguished from a viral exanthem or serum sickness-like reaction.

Familial Cold Autoinflammatory Syndrome; FCAS

Genes/gene map loci involved in inheritance of this condition:

Gene map locus 1q44
(www.ncbi.nlm.nih.gov/entrez/dispomim.
cgi?id=120100)
CIAS1

This phenotype is caused by mutation in the CIAS1 gene. In 3 unrelated families with familial cold autoinflammatory syndrome, Hoffman et al. (2001, Nature Genet. 29: 301-305) found 3 missense mutations in exon 3 of the CIAS1 gene. In 1 family with Muckle-Wells syndrome, Hoffman et al. (2001, Nature Genet. 29: 301-305) found a mutation in the CIAS1 gene, demonstrating that these 2 syndromes are indeed allelic.

Familial cold urticaria (FCU) was first described by Kile and Rusk (1940, J.A.M.A. 114: 1067-1068). After exposure to cold the patient develops urticarial wheals, pain and swelling of joints, chills, and fever.

Muckle-Wells Syndrome

Genes/gene map loci involved in inheritance of this condition:

Gene map locus 1q44

(www.ncbi.nlm.nih.gov/entrez/dispomim.cgi?id=191900)

CIAS1

The phenotype of this disease is caused by mutations in the CIAS1 gene. In a family with Muckle-Wells syndrome, Hoffman et al. (2001, Nature Genet. 29, 301-305) found a mutation in the CIAS1 gene. Hoffman et al. (2001, Nature Genet. 29, 301-305) also found mutations in the CIAS1 gene causing familial cold autoinflammatory syndrome, thus demonstrating that these 2 disorders are allelic.

Muckle and Wells (1962, Quart. J. Med. 31, 235-248) described a family in which urticaria, progressive perceptive deafness, and amyloidosis were combined in a dominantly inherited syndrome. Five generations were affected. Autopsy in 2 patients showed absent organ of Corti, atrophy of the cochlear nerve, and amyloid infiltration of the kidneys. Amyloidosis is a complication of urticaria due to cold sensitivity Black (1969, Ann. Intern. Med. 70, 989-994) described affected persons in 3 generations of a family and emphasized limb pains as a feature. Gerbig et al. (1998, Quart. J. Med. 91, 489-492) stated that about 100 cases of the urticaria-deafness-amyloidosis syndrome had been reported since the description of the syndrome in 9 members of a Derbyshire family by Muckle and Wells (1962, Quart. J. Med. 31, 235-248).

Ankylosis Spondylitis, Bechterew Syndrome

Genes/gene map loci involved in inheritance of this condition:

Gene map locus 6p21.3, 6p21.3

(www.ncbi.nlm.nih.gov/Omim/getmap.cgi?1106300)

AS, ANS (Ankylosing spondylitis), HLA-B (Major histocompatibility complex, class I, B)

There is evidence that the HLA-B27 allele is associated with susceptibility to ankylosing spondylitis. Karten et al. (1962, Arthritis Rheum. 5, 131-143) demonstrated familial aggregation. Rheumatoid arthritis and positive tests for rheumatoid factor were found no more often in the relatives of spondylitics than in those of controls, suggesting that rheumatoid arthritis and ankylosing spondylitis are distinct entities. De Blecourt et al. (1961, Ann. Rheum. Dis. 20, 215-220) found spondylitis 22.6 times more frequently in the relatives of spondylitic patients than in the relatives of controls. They suggested autosomal dominant inheritance with greater penetrance in males than in females. O'Connell et al. (1959, Ann. Intern. Med. 50, 1115-1121) arrived at the same conclusion. The familial incidence was higher when the proband was female. Kornstad and Kornstad (1960, Acta Rheum. Scand. 6, 59-64) described 2 families in which only females were affected. Emery and Lawrence (1967, J. Med. Genet. 4, 239-244) presented data that they interpreted as indicating multifactorial inheritance, however. Linkage data were published by Kornstad and Kornstad (1960, Acta Rheum. Scand. 6, 59-64) and earlier by Riecker et al. (1950, Ann. Intern. Med. 33, 1254-1273). Schlosstein et al. (1973, New Eng. J. Med. 288, 704-706) found HLA specificity w27 in 35 of 40 cases (87.5%) of ankylosing spondylitis and in only 8% of normal controls. The TLA findings brought thinking about the genetics full-circle. Autosomal dominant inheritance with reduced penetrance seemed to be established.

Lupus Erythematosus, Systemic, SLE

Genes/gene map loci involved in inheritance of this condition:

Gene map locus 1q41-q42, 1q23, 1q23, 12q24, 11q14, 4p16-p15.2, 2q37.3

(www.ncbi.nlm.nih.gov/Omim/getmap.cgi?1152700)

FCGR3A, FCGR2A, CD16, IGFR3, TNFSF6, APT1LG1, FAS, FASL, SLEB1 (Systemic lupus erythematosus, susceptibility to, 1), SLE1, PDCD1 (Programmed cell death 1), SLEB2 (Systemic lupus erythematosus, susceptibility to, 2), SLEB3 (Systemic lupus erythematosus, susceptibility to, 3), SLEH1 (Systemic lupus erythematosus with hemolytic anemia, susceptibility to, 1), SLEB4 (Systemic lupus erythematosus, susceptibility to, 4), SLEV1, SLEN1, SLEN2, SLEN3, DNAse1

There is evidence that multiple genes influence susceptibility to human SLE. These include the gene encoding immunoglobulin G Fc receptor II (FCGR2A) on 1q23. Linkage to 1q41 has been identified in African American families (SLEB1) and to 4p in European American families (SLEB3). Another locus has been mapped to chromosome 2q (SLEB2); a single-nucleotide polymorphism in the PDCD1 gene has been identified as the basis of susceptibility to this form. A locus for susceptibility to SLE associated with vitiligo has been mapped to 17p13 (SLEV1). Susceptibility to SLE with hemolytic anemia as an early or prominent clinical manifestation shows linkage to 11q14 (SLEH1). Susceptibility to SLE associated with nephritis has been linked to chromosomes 10q22.3 (SLEN1), 2q34-q35 (SLEN2), and 11p15.6 (SLEN3). There seems to be a direct connection between development of SLE and low activity of DNAse1.

Systemic lupus erythematosus (SLE), a chronic, remitting, relapsing, inflammatory, and often febrile multisystemic disorder of connective tissue, acute or insidious at onset, is characterized principally by involvement of the skin, joints, kidneys, and serosal membranes. Lupus erythematosus is thought to represent a failure of the regulatory mechanisms of the autoimmune system.

The pathogenesis of SLE is multifactorial and polygenic. The apoptosis genes FAS and FASL are candidate contributory genes in human SLE, as mutations in these genes result in autoimmunity in several murine models of this disease. In humans, FAS mutations result in a familial autoimmune lymphoproliferative syndrome. Wu et al. (1996, J. Clin. Invest. 98, 1107-1113) studied DNA from 75 patients with SLE using SSCP analysis for potential mutations of the extracellular domain of FASL. In 1 SLE patient who exhibited lymphadenopathy, they found an 84-bp deletion within exon 4 of the FASL gene, resulting in a predicted 28-amino acid in-frame deletion.

Skin Disorders

In a specific embodiment, the disease to be treated or prevented is a skin disorder. The inherited condition referred to above may affect the skin. The medicament or pharmaceutical composition may be administered topically. In a particular embodiment, the medicament or pharmaceutical composition may be administered topically to the skin of an individual.

When the disorder to be treated or prevented is a skin disorder, and/or when the inherited condition affects the skin, the medicament may be administered in accordance with the following embodiments.

The medicament to be administered may be a topical pharmaceutical composition for the prevention or treatment of skin disorders, comprising:

(i) at least about 0.1% of an active agent selected from the group consisting of HDAC inhibitors, 2-PPA and pharmaceutically acceptable salts thereof, derivatives of 2-PPA and pharmaceutically acceptable salts thereof, and (ii) a dermatologically acceptable carrier.

The term "topical application", as used herein, means to apply or spread the compositions of the present invention onto the surface of the skin. The term "dermatologically acceptable," as used herein, means that the compositions or components thereof so described are suitable for use in contact with human skin without undue toxicity, incompatibility, instability, allergic response, and the like.

Unless indicated otherwise, percentage values given herein are % by weight (w/w).

The compositions for topical use preferably comprise from about 0.1% to about 25%, more preferably from about 0.1% to about 6%, even more preferably from about 0.3% to about 5%, still more preferably from about 0.5% to about 4%, still more preferably from about 1% to about 4%, most preferably from about 2% to about 4%, of the active agent.

2-PPA may be topically applied once to three times daily at an accumulated total daily dose of 0.5 mg (milligram) to 10 mg (milligram) per lesion of approximately 1 $cm^2$ (qcm). In a more preferred embodiment, 2-PPA is used topically applied once to three times daily at an accumulated total daily dose of 1 mg (milligram) to 8 mg (milligram) per lesion of approximately 1 $cm^2$ (qcm). In an even more preferred embodiment, 2-PPA is used topically applied once to three times daily at an accumulated total daily dose of 2 mg (milligram) to 6 mg (milligram) per lesion of approximately 1 $cm^2$ (qcm). The actual daily dose depends on the size of the lesion treated, and accordingly increases with increased lesion size, including lesion sizes of up to approximately 100 $cm^2$ (qcm) with according increases of daily doses.

The compositions for topical use usually comprise from about 1% to about 99.9% of a dermatologically acceptable carrier within which the composition is incorporated to enable the active agent, as well as other optional actives, to be delivered to the skin at an appropriate concentration. In a preferred embodiment the composition for topical use is a semisolid at 25° C. and under atmospheric pressure. In accordance with this embodiment, the product form of the composition may be a cream, an ointment, a gel or a paste. The product form of the composition may be a liquid dispersion, e.g. a lotion.

In another aspect of the invention the composition further comprises retinoic acid or a derivative thereof The concentration of retinoic acid or the derivative in the composition is preferably from about 0.01% to about 1%, more preferably from about 0.05% to about 0.5% of the composition. The retinoid is preferably selected from the group consisting of 9-cis retinoic acid, trans-retinoic acid, all-trans retinoic acid and Tazarotene.

In yet another aspect of the invention the composition further comprises a chemotherapeutic drug such as 5-Fluorouracil. The concentration of the chemotherapeutic drug preferably is from about 0.1% to about 10%, more preferably from about 1% to about 10% of the composition.

In a preferred embodiment, the carrier is not a solution. In another preferred embodiment, the carrier is a cream, a paste, an ointment, a lotion or a gel.

Another aspect of the invention is the use of a HDAC inhibitor, e.g. 2-PPA, a pharmaceutically acceptable salt thereof, a derivative of 2-PPA or a pharmaceutically acceptable salt thereof, for the manufacture of a medicament for the prevention or treatment of a skin disorder wherein a medicament comprising at least about 0.1% 2-PPA or derivative thereof is topically applied to the skin of an individual in need thereof.

The skin disorder preferably is a disease of the human skin in which induction of hyperacetylation of proteins has a beneficial therapeutic effect for patients. The skin disorder may be a skin tumor, e.g., Basal Cell Carcinoma, Squamous cell carcinoma, Keratoakantoma, Bowen disease and cutaneous T-Cell Lymphoma. The skin disorder may be a pre-neoplastic skin disease such as Actinic keratosis. In other embodiments, 2-PPA or its derivative may be used for the treatment of inflammations of the skin and/or mucosa. Non-limiting examples of inflammations of the skin and/or mucosa are Psoriasis, Ichtiosis and Acne.

Administration of 2-PPA or the derivative thereof according to the present invention may be combined with an established anti-cancer therapy. 2-PPA or the derivative thereof and the established cancer therapy may be applied simultaneously or successively (at different time points). Further optional actives may be used in the treatment according to the invention. 2-PPA or the derivative thereof and the further active may be administered simultaneously or successively (at different time points). Further actives include inhibitors of histone deacetylases which are different to 2-PPA, including but not limited to compounds such as NVP-LAQ824 (Novartis), Trichostatin A, Suberoyl anilide hydroxamic acid (Aton), CBHA (ATON), Pyroxamide (Aton), Scriptaid (Johns Hopkins), CI-994 (Pfizer), CG-1521 (CircaGen), Chlamydocin (Janssen), Biaryl hydroxamate, e.g., A-161906 (Abbott), Bicyclic aryl-N-hydroxycarboxamides (Kansai University), PXD-101 (Prolifix), Sulfonamide hydroxamic acid (MethylGene), TPX-HA analogue (CHAP) (Japan Energy), Oxamflatin, Trapoxin, Depudecin, Apidicin (Kyongji), benzamides such as MS-27-275 (Mitsui), pyroxamides and derivatives therof, short chain fatty acids such as butyric acid, and derivatives thereof, e.g., Pivanex (Pivaloyloxymethyl butyrate), cyclic tetrapeptides such as trapoxin A, Depsipeptide (FK-228; Fujisawa/NCI) and related peptidic compounds, Tacedinaline (Pfizer), MG2856 (MethylGene), and HDAC class III inhibitors or SIRT inhibitors (see Kelly, O'Connor and Marks, 2002; Expert Opin. Investig. Drugs 11 (12), 1695-1713).

Administration of 2-PPA or the derivative thereof may be combined with administration/application of chemotherapeutic or cytotoxic drugs (e.g. 5-FU), differentiation inducing drugs (e.g. vitamin D, vitamin D derivatives, retinoids, receptor binding agents such as imiquimode), radiation therapy (e.g. x-rays or gamma rays), immunological approaches (antibody therapy, vaccination), combined immunotherapeutic/ cytotoxic approaches (e.g. antibodies conjugated with cytotoxic components), anti-angiogenesis approaches, and the like.

In a further embodiment, 2-PPA or its derivative potentiates orally applied retinoid activity in neoplastic and nonneoplastic skin diseases including skin tumors; Basal Cell Carcinoma; Squamous cell carcinoma; Keratoakantoma; Bowen disease; cutaneous T-Cell Lymphoma; Actinic keratosis; Psoriasis; Ichtiosis; Acne; other inflammatory skin diseases by topical application of 2-PPA alone.

Formulation

The topical compositions may comprise from about 1% to about 99.9% of a dermatologically acceptable carrier within which the compositions of the present invention is incorporated to enable the active agent, as well as other optional actives, to be delivered to the skin at an appropriate concentration.

The carrier may contain one or more dermatologically acceptable solid, semi-solid or liquid fillers, diluents, solvents, extenders and the like. The carrier may be solid, semisolid or liquid. Preferred carriers are substantially semi-solid.

The carrier can itself be inert or it can possess dermatological benefits of its own. Concentrations of the carrier can vary with the carrier selected and the intended concentrations of the active agent and optional components.

Suitable carriers include conventional or otherwise known carriers that are dermatologically acceptable. The carrier should also be physically and chemically compatible with the essential components described herein, and should not unduly impair stability, efficacy or other use benefits associated with the compositions of the present invention. Preferred components of the compositions of this invention should be capable of being comingled in a manner such that there is no interaction which would substantially reduce the efficacy of the composition under ordinary use situations.

In another embodiment, the disease to be treated or prevented is not a skin disorder. In a further embodiment, the inherited condition referred to above does not affect the skin. In a further embodiment, the medicament or pharmaceutical composition is not administered topically. In a particular embodiment, the medicament or pharmaceutical composition is not administered topically to the skin. Other routes of administration are described herein. For example, the medicament comprising the histone deacetylase inhibitor may be administered systemically, orally, or intravenously.

Inhibitors of HDAC Enzymes

This invention also concerns the use of further histone deacetylase inhibitors for the therapy of conditions as listed above and include, but are not limited to, hydroxamic acid derivatives such as NVP-LAQ824, Trichostatin A (TSA), Suberoyl anilide hydroxamic acid, CBHA, Scriptaid, CI-994, CG-1521, Chlamydocin, Biaryl hydroxamate, e.g., A-161906, Bicyclic aryl-N-hydroxycarboxamides, PXD-101, Sulfonamide hydroxamic acid, TPX-HA analogue (CHAP), Oxamflatin, Trapoxin, Depudecin, microbial metabolites exhibiting HDAC inhibitory activity, Apidicin, benzamides such as but not limited to MS-27-27, pyroxamides and derivatives thereof, short chain fatty acids such as but not limited to butyric acid, and derivatives thereof, e.g., Pivanex (Pivaloyloxymethyl butyrate), cyclic tetrapeptides such as but not limited to trapoxin A, Depsipeptide (FK-228) and related peptidic compounds, Tacedinaline, MG2856, and HDAC class III inhibitors or SIRT inhibitors, or compounds that display HDAC isoenzyme inhibitory specificities, or compounds as provided by applicant in a recent german patent application (102 33 412.9), and also in an U.S. patent application Ser. No. (10/624,571). The formulas of these compounds are the following:

G2M-701

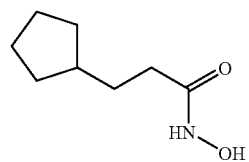

G2M-702

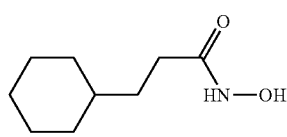

G2M-707

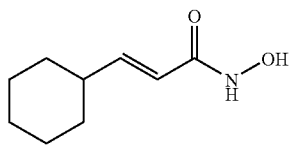

Also derivatives of 2PPA are included in this invention, but are not limited to, compounds of formula I

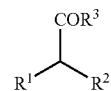

I wherein $R^1$ and $R^2$ independently are a linear or branched, saturated or unsaturated, aliphatic $C_{3-25}$ hydrocarbon chain which optionally comprises one or several heteroatoms and which may be substituted, $R^3$ is hydroxyl, halogen, alkoxy or an optionally alkylated amino group.

Different $R^1$ and $R^2$ residues give rise to chiral compounds. Usually one of the stereoisomers has a stronger teratogenic effect than the other and the more teratogenic isomer more efficiently activates PPARδ. Therefore, this isomer can be expected to inhibit HDACs more strongly (WO 02/07722 A2). The present invention encompasses the racemic mixtures of the respective compounds and in particular the more active isomers.

The hydrocarbon chains $R^1$ and $R^2$ may comprise one or several heteroatoms (e.g. O, N, S) replacing carbon atoms in the hydrocarbon chain. This is due to the fact that structures very similar to that of carbon groups may be adopted by heteroatom groups when the heteroatoms have the same type of hybridization as a corresponding carbon group.

$R^1$ and $R^2$ may be substituted. Possible substituents include hydroxyl, amino, carboxylic and alkoxy groups as well as aryl and heterocyclic groups.

Preferably, $R^1$ and $R^2$ independently comprise 3 to 10, 4 to 10 or 5 to 10 carbon atoms. It is also preferred that $R^1$ and $R^2$ independently are saturated or comprise one double bond or one triple bond. In particular, one of the side chains ($R^1$) may preferably contain $sp^1$ hybridized carbon atoms in position 2 and 3 or heteroatoms which generate a similar structure. This side chain should comprise 3 carbon or heteroatoms but longer chains may also generate HDAC-inhibiting molecules. Also, inclusion of aromatic rings or heteroatoms in $R^2$ is considered to generate compounds with HDAC inhibitory activity because the catalytic site of the HDAC protein apparently accommodates a wide variety of binding molecules. With the observation that teratogenic VPA derivatives are HDAC inhibitors, also compounds which have previously been disregarded as suitable antiepileptic agents are considered as HDAC inhibitors (WO 02/07722 A2). In particular, but not exclusively, compounds having a propinyl residue as $R^1$ and residues of 7 or more carbons as $R^2$, are considered (Lampen et al, 1999).

Preferably, the group "$COR^3$" is a carboxylic group. Also derivatization of the carboxylic group has to be considered for generating compounds with potential HDAC inhibitory activity. Such derivatives may be halides (e.g. chlorides), esters or amides. When $R^3$ is alkoxy, the alkoxy group comprises 1 to 25, preferably 1-10 carbon atoms. When $R^3$ is a mono- or di-alkylated amino group, the alkyl substituents comprise 1 to 25, preferably 1-10 carbon atoms.

In one embodiment, $R^1$ and $R^2$ independently are a linear or branched $C_{3-25}$ hydrocarbon chain which optionally comprises one double or triple bond. A preferred example of this embodiment is 4-yn-2PPA or a pharmaceutically acceptable salt thereof.

In general the present invention provides novel possibilities to treat various human diseases. Applicants found that the HDAC inhibitory and cellular differentiation-inducing activity of compounds of formula I can be used successfully alone or in combination with well established and clinically used therapeutic drugs for medical therapies. A combinatorial treatment is considered to generate superior therapeutic success in patients than the corresponding therapeutic drugs used on their own.

Aspects of the present invention include the combination of HDAC inhibitors listed in this invention with, but not restricted to, therapeutic principles currently in clinical use or in clinical development, such as

- chemotherapeutic or cytotoxic drugs (e.g. 5-FU)
- differentiation inducing drugs (e.g. vitamin D, vitamin D derivatives, retinoids, receptor binding agents such as imiquimode)
- Radiation therapy (e.g. x-rays or gamma rays)
- immunological approaches (antibody therapy, vaccination)
- combined immunotherapeutic/cytotoxic approaches (e.g. antibodies conjugated with cytotoxic components)
- anti-angiogenesis approaches.
- Others (metabolic drugs, kinase inhibitors, hormone therapy, phosphatase inhibitors, proteasome inhibitors)
- Anti-inflammatory drugs
- Dosing Specific dose levels for any particular patient may be employed depending upon a variety of factors including the age, body weight, general health, sex, diet, and prior medication, and the severity of the particular disease of the patient, and the activity of specific compounds employed, time of administration, rate of excretion, the duration of the treatment, other drugs, compounds, and/or materials used in combination. It will be appreciated that the appropriate dosage of the active compounds, and compositions comprising the active compounds, can vary from patient to patient. Determining the optimal dosage will generally involve balancing of the level of therapeutic benefit against any risk or deleterious side effects of the treatments of the conditions underlying the present invention.

Administration in vivo can be effected in one dose, continuously or intermittently throughout the course of treatment. Methods of determining the most effective means and dosages of administration are well known to those of skill in the art and will vary with the formulation used for therapy, the purpose of the therapy, the target cell being treated, and the subject being treated. Single or multiple administrations can be carried out with the dose level and pattern being selected by the treating physician.

BRIEF DESCRIPTION OF THE DRAWINGS

FIG. 1: Loss of viable cells upon treatment with 2-propylpentanoic acid (MTT tests)

FIG. 1 depicts cells with proven mutations of crucial genes which in an inherited way establish a condition which predisposes a person to develop a disorder.

FIG. 2: Treatment of mice carrying a germ line $APC^{min}$ mutation with 2-propylpentanoic acid leads to a reduced number of colorectal adenomas.

FIG. 2 shows results from a $APC^{min}$ mouse model. Treatment of $APC^{min}$ mice for 4 weeks with 2PPA or Celebrex led to reduction in the number of colorectal adenomas. Celebrex treated mice showed an intensely inflated stomach, small intestine, and colon compared to mice treated with PBS or 2PPA.

FIG. 3 shows mRNA expression modulation of immunologically relevant genes such as inflammatory cytokines by HDAC inhibitors after stimulation with LPS or PMA/Ion (Example 3).

FIG. 4 shows mRNA expression modulation of immunologically relevant genes such as inflammatory cytokines by HDAC inhibitors after stimulation with PMA/Ion (Example 3).

FIG. 5 shows mRNA expression modulation of immunologically relevant genes such as inflammatory cytokines by HDAC inhibitors after CD3/CD28 stimulation (Example 3).

FIG. 6 shows protein expression modulation of immunologically relevant genes such as inflammatory cytokines by HDAC inhibitors after CD3/CD28 stimulation (Example 3).

FIG. 7 shows protein expression modulation of immunologically relevant genes such as inflammatory cytokines by HDAC inhibitors (Example 3).

FIG. 8 shows a clinical therapy schedule using the HDAC inhibitor 2PPA in a cancer patient (Example 4).

FIG. 9 shows the successful induction of histone acetylation and down regulation of the HDAC-2 protein in periperal blood cells of a patient treated with the HDAC inhibitor 2PPA according to the treatment schedule depicted in FIG. 8 (Example 4).

FIG. 10 shows the successful mRNA and protein expression modulation of immunologically relevant genes such as inflammatory cytokines by using the HDAC inhibitor 2PPA in a patient according to the treatment schedule depicted in FIG. 8 after CD3/CD28 stimulation (Example 4).

DETAILED DESCRIPTION OF EXEMPLARY EMBODIMENTS

Examples

Example 1

Figure 3:
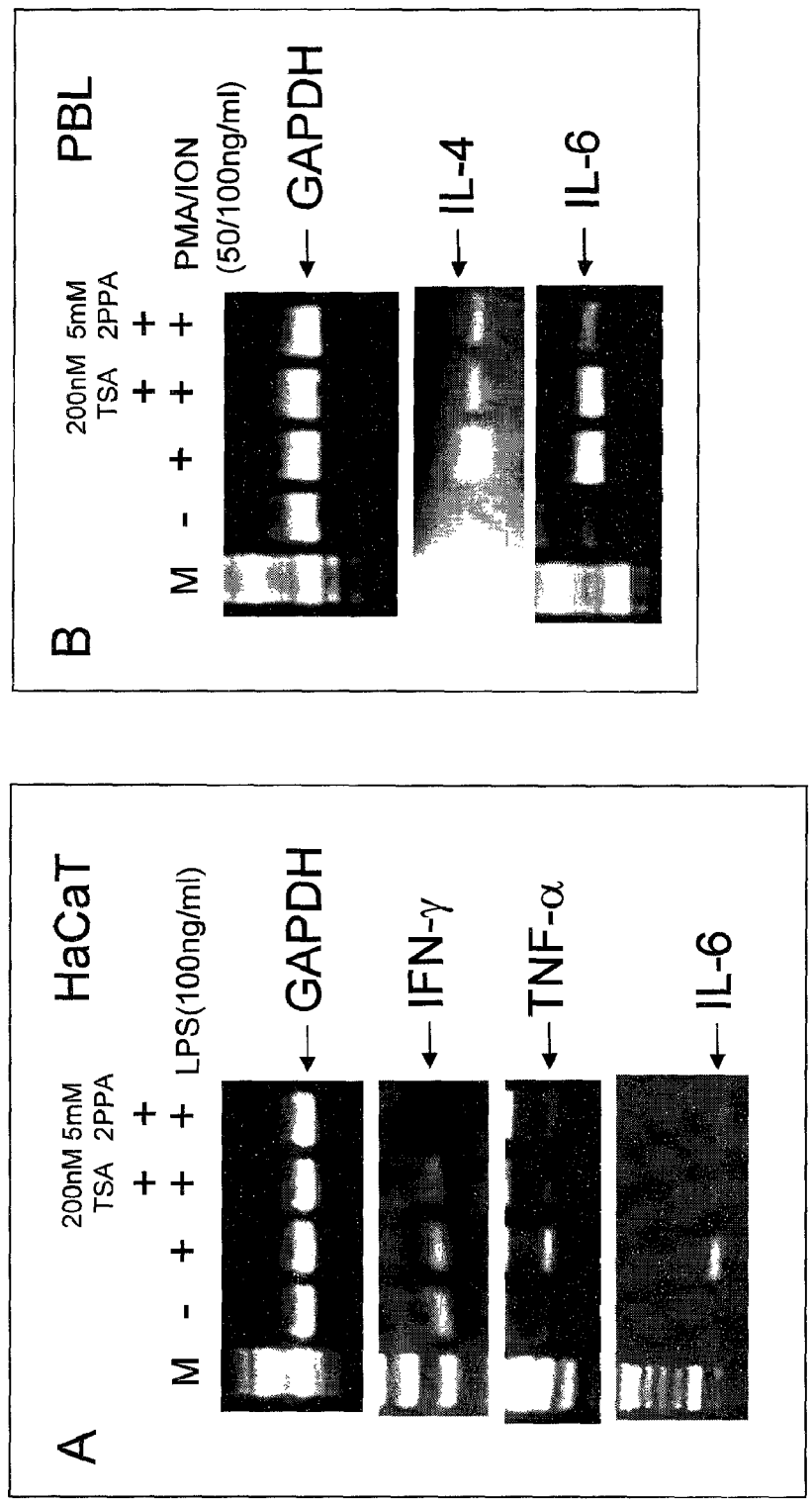
FIG. 3: Modulation of inflammatory cytokines by TSA and 2PPA in human keratinocytes and peripheral blood lymphocytes.

Data on the inhibitory activity by 2PPA on cells that harbour mutations or polymorphisms in gene loci frequently found to be inherited in predisposing conditions in men.

Loss of viable cells upon treatment with 2-propyl pentanoic acid (MTT tests).

Methods:
Cell Lines and Cell Culture

In FIG. 1 cell lines are listed with proven mutations of crucial genes which in an inherited way establish a condition that predisposes a person to develop a disorder. The cells were grown in the respective medium as described in FIG. 1.

Cell viability assays

The cell lines listed in table 1 were seeded in 96 well plates at a density of $1 \times 10^4$ cells/well in normal growth medium. 2-propyl pentanoic acid was added at final concentrations between 0.5 and 3 mM to triplicate samples and the cells were incubated for 40 h to 70 h. Control cells were grown in the absence of 2-propyl pentanoic acid. Ten µl of 10 mg/ml 3-(4,5-dimethylthiazole-2-yl)-2,5 diphenyltetrazolium bromide (MTT) (Sigma, Deisenhofen, Germany) in PBS were added to each well and the cells were incubated for another 3 h. Cells were lysed by the addition of 90 µl of lysis buffer (20% SDS in 50% dimethyl formamide, pH 4.7). After solubilization of the formazan product, the absorption at 590 nm was determined in a microplate reader (Dynatech, Denkendorf, Germany) and the relative amount of viable cells in comparison to cells grown without the addition of 2-propyl pentanoic acid was determined.

Results:

In all the cell lines tested, treatment with 2-propyl pentanoic acid resulted in a 20-80% inhibition of cell viability. These results demonstrate that 2-propyl pentanoic acid potently reduces the number and/or viability of a wide variety of cell lines representing inherited predisposing conditions which are linked to genetically inherited mutations of crucial genes that predispose the carrier to develop the disease phenotype. The loss of viability could indicate a reduction in cell number upon induction of cell death and/or induction of cellular differentiation associated cell cycle arrest. This induction of differentiation and/or cell death suggests that 2-propyl pentanoic acid and derivatives thereof could be used for the therapy of such inherited predisposing conditions.

Example 2

Treatment of mice carrying a germ line $APC^{min}$ mutation with 2-propyl pentanoic acid leads to a reduced number of colorectal adenomas.

Methods:
Animal experiments

Ten to sixteen weeks old age- and sex-matched heterozygous C57BL/6J-$APC^{min}$ mice (Jackson Laboratories, Bar Harbor, Me.) were either left untreated or were treated with 2-PPA or Celecoxib. Control animal were injected (i.p.) with PBS. 2-PPA was injected as isotonic aequous solution of the sodium salt (2×400 mg/kg/day) for four weeks, while Celecoxib was fed to the animals ad libidum at 1250 ppm (0, 12%) for four weeks. At necropsy entire intestinal tracts were opened longitudinally and fixed in 10% phosphate buffered formaldehyde for 24 h. Polyp contrast was increased performing a 1 min staining in 0.1% methylene blue prior to determination of polyp numbers and sizes under a dissecting microscope by two independent observers unaware of the treatment that the mice had received.

Results:

A genetic link to inappropriate function of the transcriptional repression machinery could be established in solid tumors: loss of the adenomatosis polyposis coli (APC) tumor suppressor and increased signalling through the Wnt/β-catenin pathway induce HDAC-2 expression. Increased HDAC-2 expression on the other hand is found in the majority of human colon cancer explants as well as in intestinal mucosa and polyps of $APC^{min}$ mice. HDAC-2 is required and sufficient on its own to prevent apoptosis of colonic cancer cells. Interference with HDAC-2 activity by 2-PPA reduces adenoma formation in $APC^{min}$ mice pointing towards HDAC-2 as a particularly relevant potential target in tumor therapy.

As depicted in FIG. 2A treatment of $APC^{min}$ mice with 2-PPA as well as Celecoxib for four weeks clearly reduces the number of adenomas in the small intestine.

Even though primary adenoma burden in human beings is mainly located in the colon, Celecoxib has shown efficacy in the treatment of colorectal polyps in patients suffering from Familial Adenomatous Polyposis (FAP). This supports that results obtained using the $APC^{min}$ mouse model are also indicative for the treatment of FAP in human beings. Taken together, these results clearly suggest that 2-PPA may be used as a very effective therapeutic agent to suppress the formation of colorectal polyps in FAP patients.

Celecoxib as a COX-2 inhibitor has been described to have severe side effects such as intestinal bleeding. As can be seen in FIG. 2B, in our $APC^{min}$ mice treated with Celecoxib exhibited an intensely inflated stomach, small intestine, and colon. Mice treated with 2-PPA on the other hand did not show any abnormalities in the gastrointestinal tract. In summary, 2-PPA may be used as a very potent therapeutic agent for treatment and suppression of the inherited chronic disease FAP.

Example 3

Modulation of the expression of immunologically relevant proteins such as inflammatory cytokines. Treatment of human immortalized keratinocytes and peripheral blood lymphocytes with different HDAC inhibitors results in a reduction of inflammatory cytokines (FIGS. 3 to 7).

Methods:
Isolation of Total RNA from Human Immortalized Keratinocytes

Human immortalized keratinocytes (HaCaT cells) were seeded at a density of 2.5 million cells per ml into 75 cm² flasks. Cells were either left untreated or preincubated with 200 nM trichostatin A (TSA) or 5 mM 2-propyl-pentanoic acid (2PPA) for 4 hours at 37° C. followed by subsequent stimulation with lipopolysaccharide (LPS) (100 ng/ml). After 24 hours at 37° C. cells were lysed and total RNA was isolated using the RNeasy mini kit from Qiagen.

Isolation and Treatment of Peripheral Blood Mononuclear Cells

Monocyte and macrophage depleted peripheral blood mononuclear cells were obtained from consenting adults via separation using Ficoll-Hypaque. The peripheral blood mononuclear cells (PBMC) fraction was washed and seeded in 9 cm petri dishes. After an incubation of 2 hours at 37° C. to remove most of the monocytes, macrophages, and B-cells, the non-adherent cells were collected and cultured in 175cm² flasks for 2 days. Cells were harvested and adjusted to 3 million cells per ml. Aliquots of 500μl were transferred to each well of 24-well flat bottom plates. Peripheral blood lymphocytes (PBL's) were treated with various concentrations of HDAC inhibitors as indicated. After a 2 hour incubation time at 37°C cells were stimulated with phorbol 12-myristate 13-acetate (PMA) / ionomycin (Ion) or activated via T cell receptor (TCR/CD3) complex with 10μg/ml anti-CD3 mAb (OKT3) and 2.5μg/ml anti-CD28 mAb. After 24 hours at 37° C. the supernatant was removed and frozen for cytokine assays. Cell pellets were lysed and total RNA was isolated using the RNeasy mini kit from Qiagen.

RT-PCR and Semiquantitative PCR

One microgram of total RNA was transcribed to cDNA by standard methods using reverse transcriptase and an oligo-dT primer (Invitrogen). For semiquantitative PCR, 2 μl of cDNA was amplified by PCR using specific primers. Primers for PCR were synthesized by MWG and are as follows:

```
GAPDH:
5'-GGTGAAGGTCGGAGTCAACG-3'          (SEQ ID NO: 1)
and

5'-CAAAGTTGTCATGGATGACC-3';         (SEQ ID NO: 2)

IL-2:
5'-ATGTACAGGATGCAACTCCT-3'          (SEQ ID NO: 3)
and

5'-TCAAGTTAGTGTTGAGATGA-3';         (SEQ ID NO: 4)

IL-4:
5'-ATGGGTCTCACCTCCCAACT-3'          (SEQ ID NO: 5)
and

5'-TCAGCTCGAACACTTTGAAT-3';         (SEQ ID NO: 6)

IL-5:
5'-ATGAGGATGCTTCTGCATTTGAG-3'       (SEQ ID NO: 7)
and

5'-TCCACTCGGTGTTCATTACACC-3';       (SEQ ID NO: 8)

IL-6:
5'-ATGAACTCCTTCTCCACAAGCGCC-3'      (SEQ ID NO: 9)
and

5'-CTACATTTGCCGAAGAGCCCTCAG-3';     (SEQ ID NO: 10)

IL-8:
5'-ATGACTTCCAAGCTGGCCGTGGC-3'       (SEQ ID NO: 11)
and

5'-TTATGAATTCTCAGCCCTCTTC-3';       (SEQ ID NO: 12)

IL-10:
5'-TTGCCTGGTCCTCCTGACTG-3'          (SEQ ID NO: 13)
and

5'-GATGTCTGGGTCTTGGTTCT-3';         (SEQ ID NO: 14)

IL-12:
5'-ATGTGTCACCAGCAGTTGGTCATC-3'      (SEQ ID NO: 15)
and

5'-CTATAGTAGCGGTCCTGGGC-3';         (SEQ ID NO: 16)

TNF-α:
5'-ATGAGCACTGAAAGCATGATCCGG-3'      (SEQ ID NO: 17)
and

5'-TCACAGGGCAATGATCCCAAAG-3';       (SEQ ID NO: 18)

IFN-γ:
5'-ATGAAATATACAAGTTATATCTTGGCTTT-3' (SEQ ID NO: 19)
and

5'-TTACTGGGATGCTCTTCGAC-3'.         (SEQ ID NO: 20)
```

IL-2 and TNF-α ELISA

To perform ELISA's, supernatants of treated and untreated PBL's were collected and IL-2 as well as TNF-α were measured using the Duo Set ELISA Development System (R&D Systems) as described by the manufacturer.

Western Blot

Whole cell extracts were prepared by lysis of cells in lysis buffer including protease inhibitors. Lysates were separated by SDS gel electrophoresis and transferred onto PVDF membranes. Acetylated histones H3 and H4 were detected by western blot analysis using an anti-acetylated H3 antibody (Upstate, #06-942), an anti-acetylated H4 antibody (clon T25; patent application EP 02.021984.6) and anti-β-actin antibody. The β-actin antibody was used as a control for equal loading.

Results:

Treatment of cells with TSA and other HDAC inhibitors leads to histone hyperacetylation and modulation of transcription. Therefore, we studied the effect of TSA and other HDAC inhibitors on the expression level of cytokine mRNA by semi-quantitative RT-PCR analysis and cytokine secretion by ELISA.

Human immortalized keratinoyctes (HaCaT) were cultured for 24 hours in the absence or presence of TSA or 2PPA, respectively. After a preincubation of 4 hours with the HDAC inhibitors, LPS was used to induce cytokine production. The level of cytokine mRNA expression is shown by semi-quantitative RT-PCR (FIG. 3). Agarose gel electrophoresis of the RT-PCR products showed a significant decrease in the level of TNF-α and IL-6 mRNA in TSA and 2PPA treated cells compared to untreated, but stimulated control (FIG. 3A). Under these conditions GAPDH mRNA as internal control remained unaffected. Although, the induction of IFN-γ by LPS stimulation was only moderate, the mRNA transcript of IFN-γ was virtually unaffected by exposure to TSA, but significantly reduced by 2PPA.

Similar results were obtained using peripheral blood lymphocytes (PBLs) (FIG. 3B). Isolated PBL's were preincubated with TSA and 2PPA for 2 hours followed by stimulation with PMA/Ion for 24 hours at 37° C. FIG. 3B shows the effect of TSA and 2PPA on IL-4 and IL-6 mRNA transcripts. TSA as well as 2PPA significantly reduced PMA/Ion mediated stimulation of IL-4. While only moderate effects were found on IL-6 mRNA after TSA treatment, 2PPA decreased IL-6 mRNA back to the level seen in the unstimulated sample. Furthermore, FIGS. 4A and B show that other HDAC inhibitors such as suberoylanilide hydroxamic acid (SAHA), G2M-701, G2M-702, and G2M-707 can modulate cytokine expression.

Figure 4:
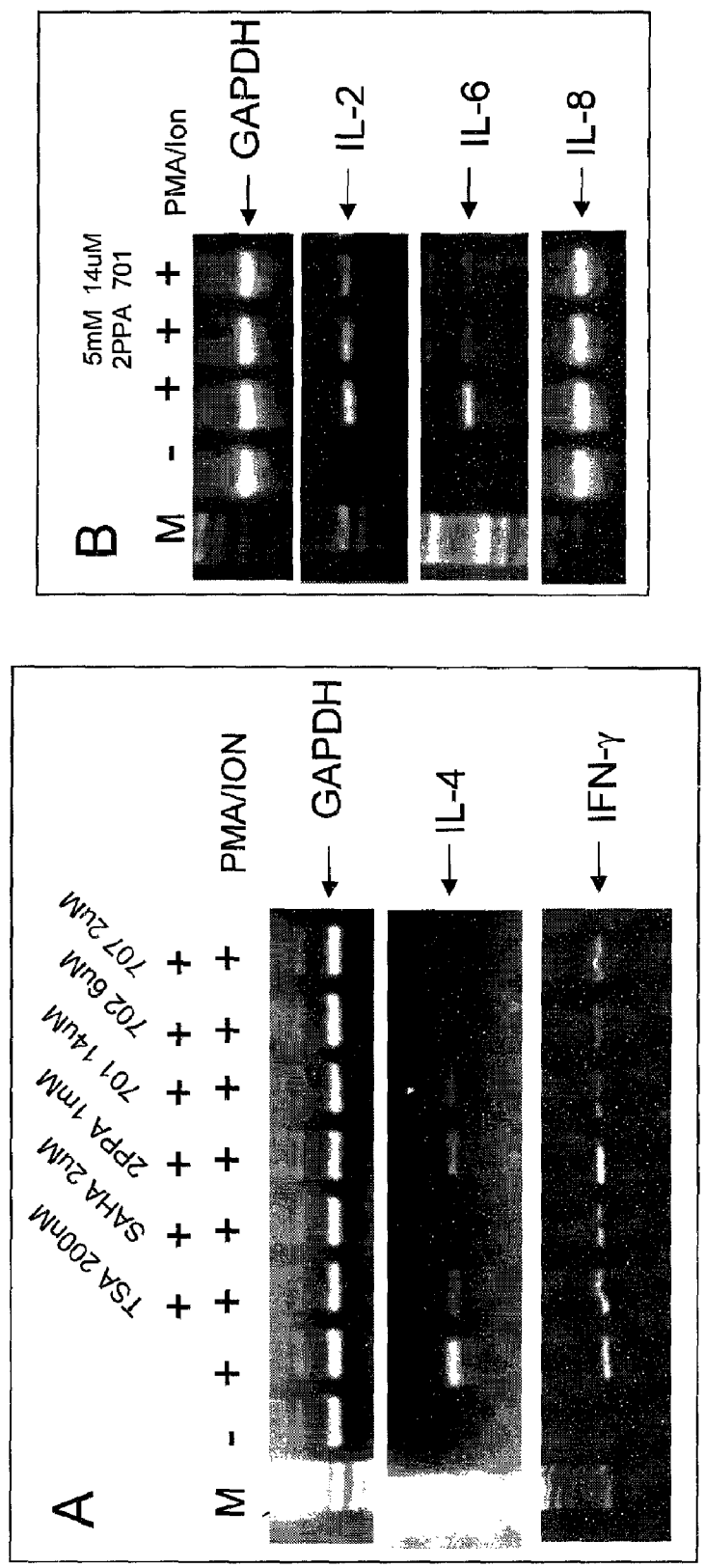
FIG. 4: Modulation of inflammatory cytokines by different HDAC inhibitors

As shown in FIG. 4, various HDAC inhibitors decreased the expression of IL-4 and IL-6 mRNA transcripts, but did not modify GAPDH mRNA expression. Under these conditions IL-8 mRNA remained stable, demonstrating that cellular activation by PMA/Ion does not modify the expression of this gene.

Figure 5:
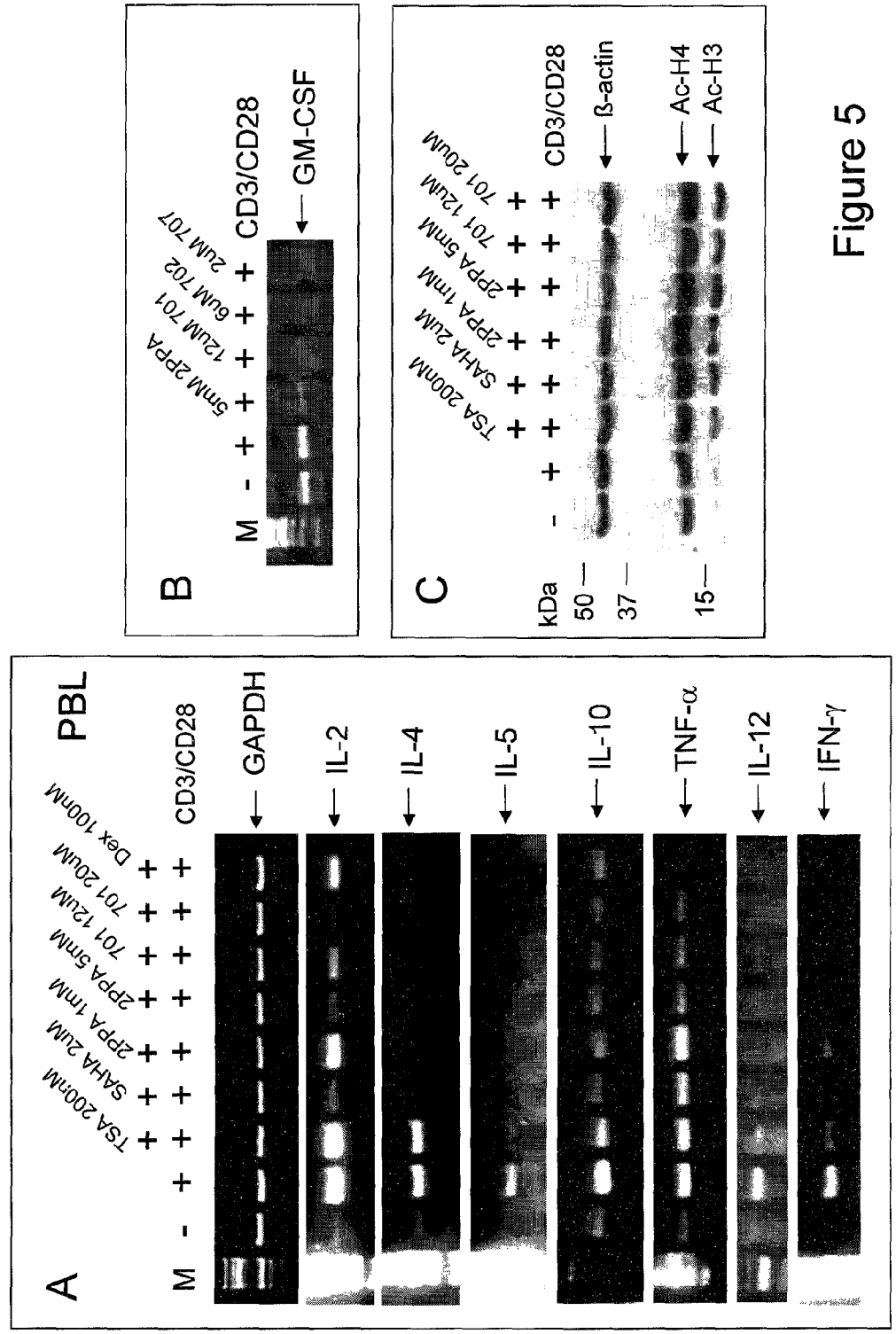
FIG. 5: Modulation of inflammatory cytokines by HDAC inhibitors in peripheral blood lymphocytes.

In comparison, the effect of HDAC inhibitors on IL-2 and IFN-γ transcription level was even more striking when T-cells were activated by the T cell receptor complex using CD3 and CD28 antibodies as shown in FIG. 5. PBL's were preincubated with the HDAC inhibitors TSA, SAHA, 2PPA, G2M-701 or the anti-inflammatory steroid Dexamethasone (Dex), 2PPA and G2M-701 were used in two different concentrations. The cells were activated via the T cell receptor complex (TCR/CD3) using CD3 and CD28 antibodies for 24 hours. As shown in FIGS. 5A and B, the mRNA transcripts of several cytokines were significantly reduced by all HDAC inhibitors used with minor differences. FIG. 5C shows a western blot analysis using antibodies against acetylated histone H3 and acetylated H4 as well as β-actin as a control for equal loading displaying the successful induction of histone hyperacetylation by HDAC inhibitors.

Figure 6:
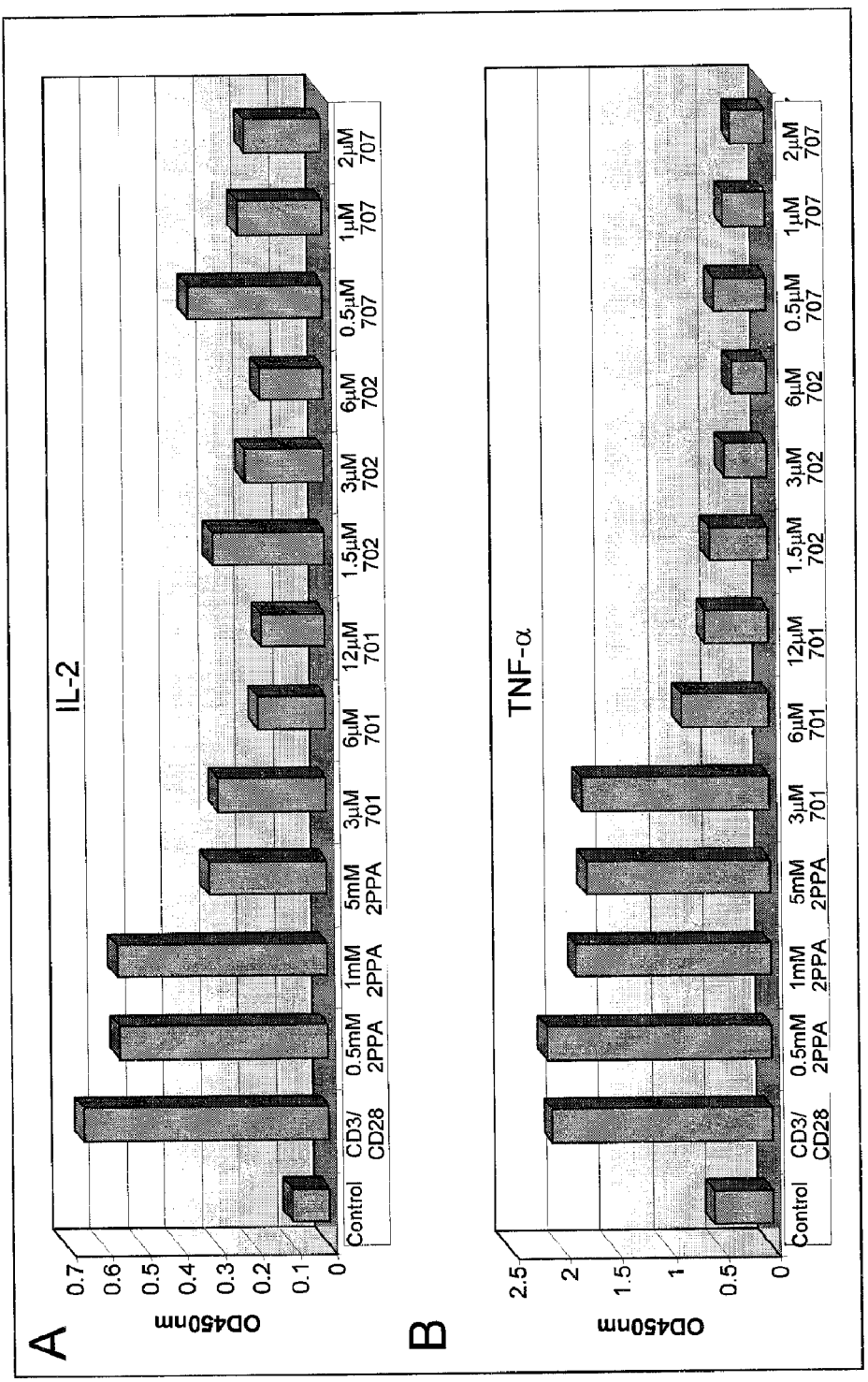
FIG. 6: Modulation of IL-2 and TNF-α expression by HDAC inhibitors in peripheral blood lymphocytes.
Figure 7:
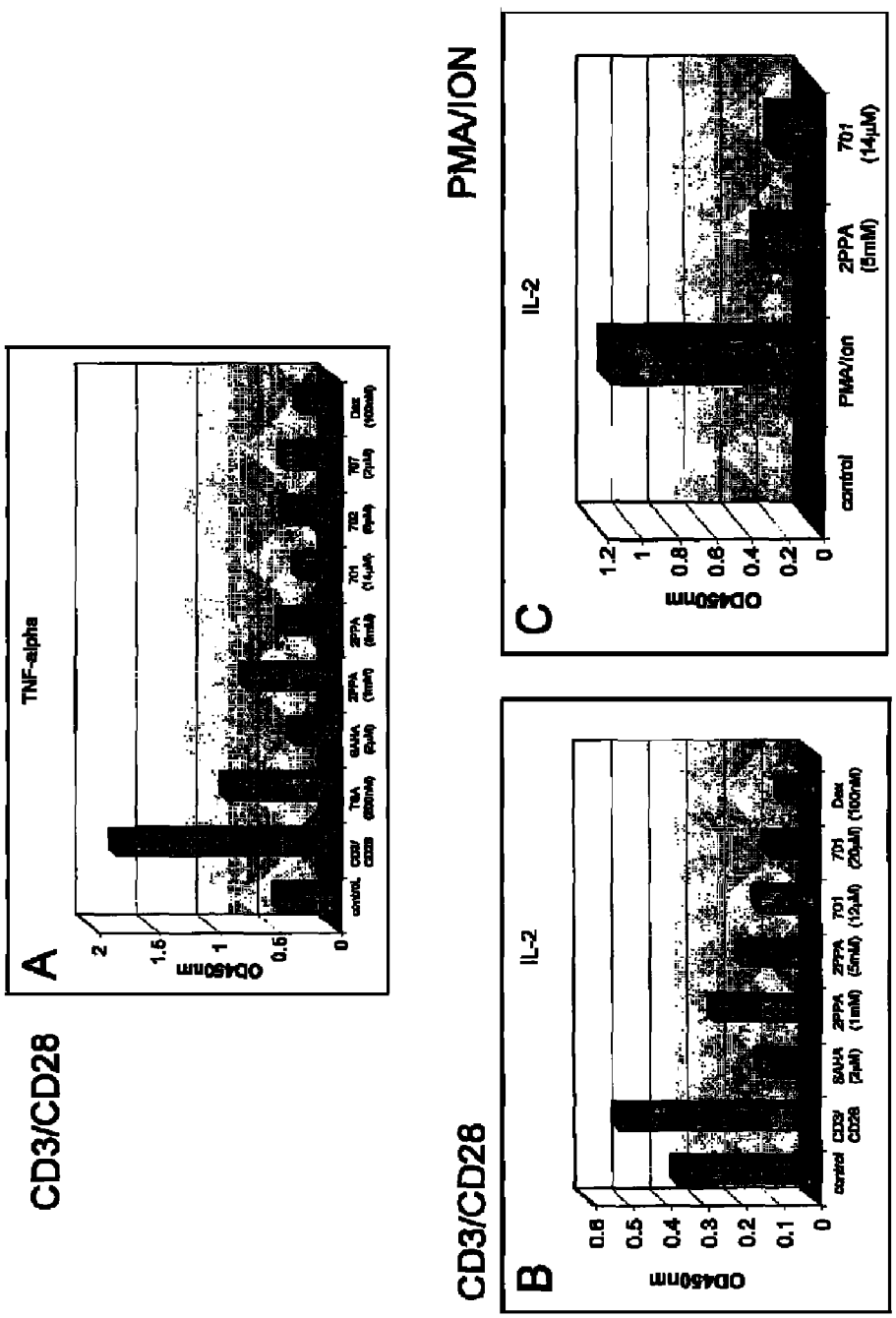
FIG. 7: Modulation of IL-2 and TNF-α expression by HDAC inhibitors in peripheral blood lymphocytes stimulated with PMA/ION and CD3/CD28 mAbs.

Similar results in consistence with experiments from semi-quantitative PCR could be obtained by analyzing secreted IL-2 and TNF-α protein levels in supernatants from PBL culture by ELISA as depicted in FIG. 6. For performing a dose-response analysis, PBL's were treated with increasing concentrations of 2PPA, G2M-701, G2M-702, and G2M-707 for two hours followed by activation with CD3 and CD28 mAbs for 24 hours at 37° C. Supernatants were collected and IL-2 as well as TNF-α secretion was quantified by ELISA. Treatment of PBL's with 2PPA, G2M-701, G2M-702, and G2M-707 resulted in a dose-dependent inhibition of IL-2 and TNF-α secretion. While 0.5 mM and 1 mM of the inhibitor 2PPA had only moderate effect, 5 mM significantly reduced the secretion of IL-2. This was even more prominent in other experiments as shown in FIG. 7 were already 1 mM of 2PPA showed a significant decrease in IL-2 as well as in TNF-α secretion. The inhibition of IL-2 and TNF-α expression was even more effective with the other HDAC inhibitors and was maximal at 6 μM of G2M-701, 3 μM of G2M-702, and 1 μM of G2M-707 (FIG. 6).

Taken together, these results demonstrated that HDAC inhibitors such as 2PPA, G2M-701, G2M-702, and G2M-707 inhibit the PMA/Ion (FIGS. 3, 4 and 7) and TCR/CD3 (FIGS. 5, 6, and 7) mediated induction of cytokine expression in human T lymphocytes and human keratinocytes.

Thus, HDAC inhibitors have the potential to modify cytokine expression in response to cellular activation. They are able to block expression of several cytokine transcripts abolishing immunologically important inflammatory cytokine production. The dramatic down-regulation of cytokine secretion by HDAC inhibitors supports their potential use as a therapeutic agent.

Example 4

Clinical Therapy Data Using an HDAC Inhibitor in Patients

2PPA, which acts as preferential inhibitor of histone deacetylase class I enzymes, induces histone hyperacetylation in cellular systems as well as in peripheral blood cells of patients.

Figure 8:
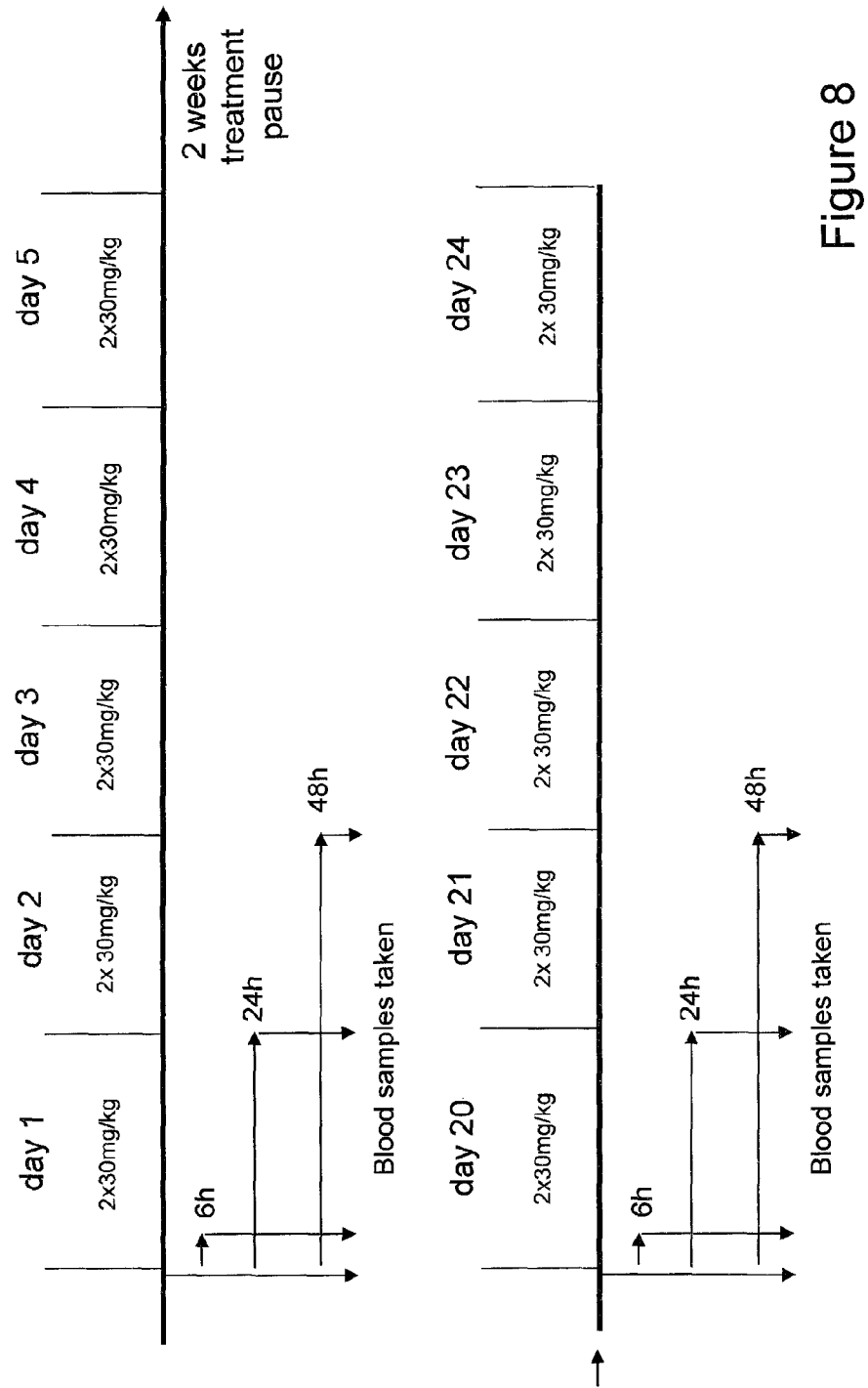
FIG. 8: 2PPA treatment schedule of a patient from a phase I/II trial
Figure 9:
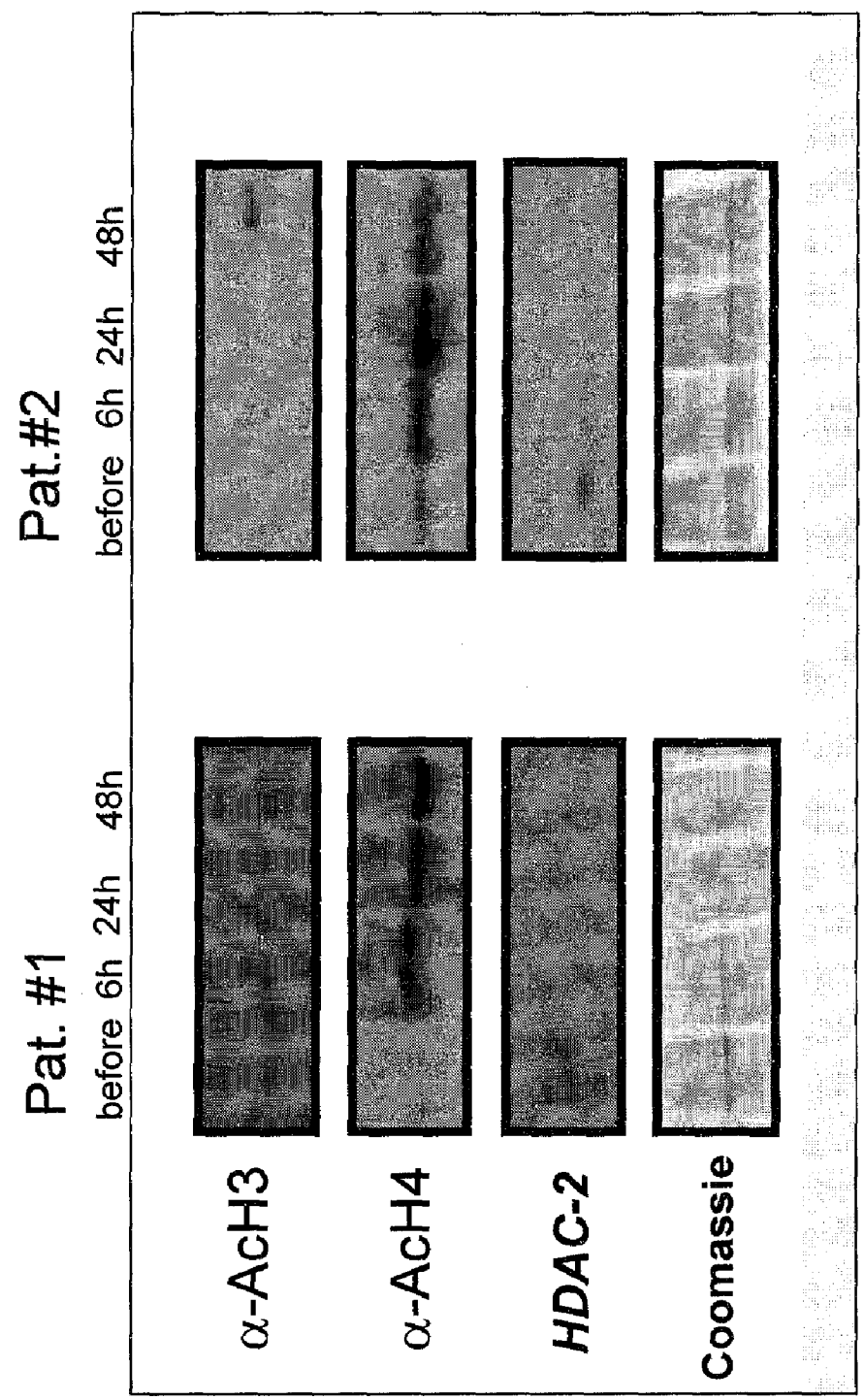
FIG. 9: 2PPA induces histone hyperacetylation and regulation of marker genes in peripheral blood from patients from a phase I/II trial.
Figure 10:
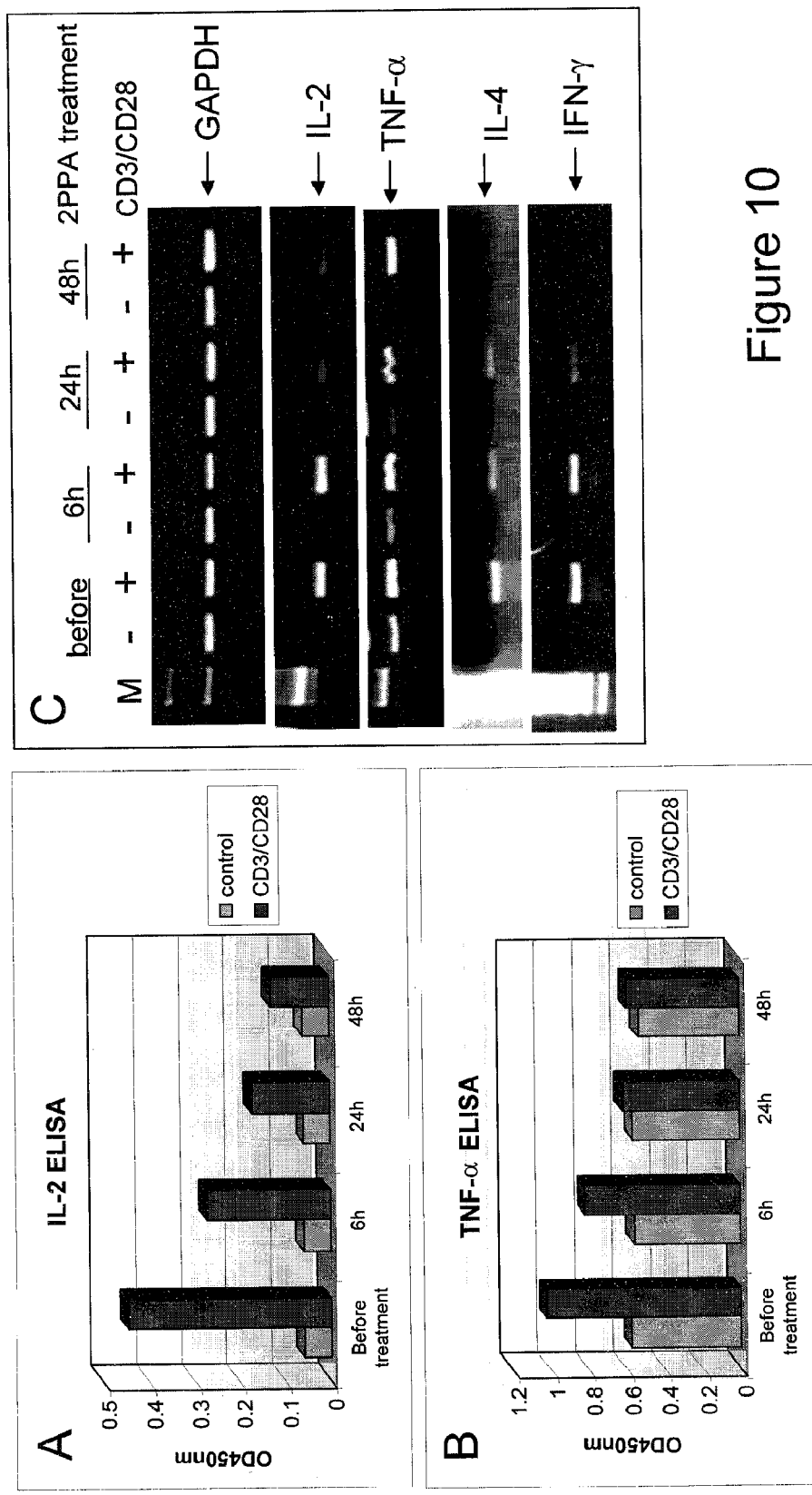
FIG. 10: Modulation of inflammatory cytokines by 2PPA from a patient in a phase I/II trial

Blood samples were taken from two patients (Pat.#1 and Pat.#2) exhibiting advanced malignant disease treated with 2PPA intravenously in the scope of a clinical Phase I/II study (FIGS. 8, 9 and 10).

Method:

Western Blot

Peripheral blood cells from patients treated with 2PPA were obtained before, 6 h, 24 h, and 48 h after start of 2PPA treatment (see treatment schedule, FIG. 8). Whole cell extracts were prepared by lysis of cells in RIPA buffer including protease inhibitors. Lysates were separated by SDS gel electrophoresis and transferred onto PVDF membranes. Acetylated histones H3 and H4 and the marker gene HDAC-2 were detected by western blot analysis using an anti-acetylated H3 antibody (Upstate, #06-942), an anti-acetylated H4 antibody (clon T25; patent application EP 02.021984.6), and an anti-HDAC-2 antibody (SCBT, SC-7899). As an equal loading control PVDF membranes were stained with Coomassie (FIG. 9).

ELISA

Peripheral blood cells from patient treated with 2PPA before, 6 h, 24 h, and 48 h after start of 2PPA treatment were seeded into a 24-well flat bottom plate with a density of 1 million cells per ml. The cells were either left unstimulated or stimulated with CD3 and CD28 antibodies. After 24 hours at 37° C. the supernatant was collected and the secretion of IL-2 and TNF-α was quantified by ELISA (R&D Systems) (FIGS. 10A and B).

RT-PCR

Total RNA from unstimulated and CD3/CD28 stimulated cells was isolated using the RNeasy mini kit (Qiagen). One microgram of total RNA was converted to cDNA by standard methods using reverse transcriptase and an oligo-dT primer (Invitrogen). For semiquantitative PCR, 2 μl of cDNA were amplified by PCR using the specific primers as described above (FIG. 10C).

Results:

The Western Blot analysis with the peripheral blood cell lysates (FIG. 9) shows the detection of Histone H3 and H4 hyperacetylation and down-regulation of the marker protein HDAC-2 with serum levels above the therapeutic plasma concentration. The induction of histone hyperacetylation and down-regulation of HDAC-2 clearly demonstrated the efficacy of the 2PPA treatment and shows that 2PPA can be used in patients to reach effective therapeutic serum concentrations inducing histone hyperacetylation in peripheral blood cells and regulation of a target gene HDAC-2. In addition, we show evidence that 2PPA modulates the expression of inflammatory cytokines such as IL-2 and TNF-α in the culture supernatant as assayed by ELISA (FIGS. 9 A, and B) consistent with a decrease in IL-2 and TNF-α mRNA transcripts in CD3/CD28 stimulated cells (FIG. 9 C). Furthermore, it significantly reduced the cytokine mRNA expression of IL-4 and IFN-γ starting at 24 hours of 2PPA treatment.

Taken together, these data show that 2PPA can efficiently modulate immunologically relevant genes such as IL-2, TNF-α, IL-4 and IFN-γ in a patient treated with the HDAC inhibitor 2PPA according to the treatment schedule depicted in FIG. 8.

Therefore, this new potential of 2PPA and other HDAC inhibitors, to act as immune modulating compounds supports this invention to employ these compounds as anti-inflammatory drugs for the therapy of disorders linked to pathologically overactive immune cells.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method of treating or suppressing colorectal polyposis in a person suffering from Familial Adenomatous Polyposis, the method comprising: administering a medicament comprising an histone deacetylase inhibitor to the person to treat or suppress colorectal polyposis.

2. The method according to claim 1, wherein the Familial Adenomatous Polyposis is based on at least one genetically inherited mutation of at least one gene, which predisposes a person to develop the phenotype of Familial Adenomatous Polyposis.

3. The method according to claim 1, wherein the Familial Adenomatous Polyposis is based on a genetically inherited polymorphism of at least one gene which predisposes the person with his/her condition to develop the phenotype of Familial Adenomatous Polyposis.

4. The method according to claim 1, wherein the Familial Adenomatous Polyposis is a predisposing disorder in which the induction of hyperacetylation of histones, of other proteins, or of both, has a beneficial therapeutic effect for patients.

5. The method according to claim 1, wherein the Familial Adenomatous Polyposis is based on a mutation or polymorphism in the APC gene.

6. The method according to claim 1, wherein the histone deacetylase inhibitor is 2-propyl-pentanoic acid or a pharmaceutical acceptable salt thereof.

7. The method according to claim 1, wherein the histone deacetylase inhibitor is selected from the group consisting of hydroxamic acid derivatives, benzamides, pyroxamides and derivatives thereof, microbial metabolites exhibiting HDAC inhibitory activity, fatty acids and derivatives thereof, cyclic tetrapeptides, peptidic compounds, HDAC class III inhibitors, and SIRT inhibitors.

8. The method according to claim 1, wherein the inhibitor of histone deacetylases is selected from the group consisting of hydroxamic acid derivatives such as NVP-LAQ824, Trichostatin A (TSA), Suberoyl anilide hydroxamic acid, CBHA, G2M-701, G2M-702, G2M-707, Pyroxamide, Scriptaid, CI-994, CG-1521, Chlamydocin, Biaryl hydroxamate, A-161906, Bicyclic aryl-N-hydroxycarboxamides, PXD-101, Sulfonamide hydroxamic acid, TPX-HA analogue (CHAP), Oxamflatin, Trapoxin, Depudecin, Apidicin, benzamides, MS-27-27, butyric acid and derivatives thereof, Pivanex (Pivaloyloxymethyl butyrate), trapoxin A, Depsipeptide (FK-228) and related peptidic compounds, Tacedinaline, and MG2856.

9. The method according to claim 1, wherein the histone deacetylase inhibitor is a compound of formula I

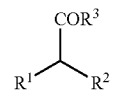

wherein $R^1$ and $R^2$ independently are a linear or branched, saturated or unsaturated, aliphatic $C_{3-25}$ hydrocarbon chain which optionally comprises one or several heteroatoms and which may be substituted, $R^3$ is hydroxyl, halogen, alkoxy or an optionally alkylated amino group, or a pharmaceutically acceptable salt thereof.

10. The method according to claim 9, wherein $R^1$ and $R^2$ independently are a linear or branched $C_{3-25}$ hydrocarbon chain which optionally comprises one double or triple bond.

11. The method according to claim 1, wherein administering comprises intraveneous, intramuscular, subcutaneous, topical, oral, nasal, intraperitoneal, or suppository based administering.

12. A method of treating Familial Adenomatous Polyposis, the method comprising: administering a medicament comprising a histone deacetylase inhibitor to an individual having Familial Adenomatous Polyposis.

13. The method according to claim 12, wherein the Familial Adenomatous Polyposis is based on a mutation or polymorphism in the APC gene.

* * * * *